US010052384B2

(12) United States Patent
Scholz

(10) Patent No.: US 10,052,384 B2
(45) Date of Patent: Aug. 21, 2018

(54) LIQUID ANTISEPTIC COMPOSITIONS CONTAINING IODINE AND A SUGAR AND/OR SUGAR ALCOHOL

(75) Inventor: Matthew T. Scholz, Woodbury, MN (US)

(73) Assignee: 3M INNOVATIVE PROPERTIES COMPANY, Saint Paul, MN (US)

(*) Notice: Subject to any disclaimer, the term of this patent is extended or adjusted under 35 U.S.C. 154(b) by 330 days.

(21) Appl. No.: 12/345,085

(22) Filed: Dec. 29, 2008

(65) Prior Publication Data
US 2009/0169647 A1 Jul. 2, 2009

Related U.S. Application Data

(60) Provisional application No. 61/018,109, filed on Dec. 31, 2007.

(51) Int. Cl.
| | |
|---|---|
| A61K 9/00 | (2006.01) |
| A61K 31/047 | (2006.01) |
| A61K 31/19 | (2006.01) |
| A61K 33/18 | (2006.01) |
| A61K 47/18 | (2017.01) |
| A61K 47/20 | (2006.01) |
| A61K 47/24 | (2006.01) |
| A61K 45/06 | (2006.01) |

(52) U.S. Cl.
CPC .......... *A61K 45/06* (2013.01); *A61K 9/0014* (2013.01); *A61K 9/0043* (2013.01); *A61K 31/047* (2013.01); *A61K 31/19* (2013.01); *A61K 33/18* (2013.01); *A61K 47/18* (2013.01); *A61K 47/20* (2013.01); *A61K 47/24* (2013.01)

(58) Field of Classification Search
CPC .. A61K 9/0014; A61K 9/0043; A61K 31/047; A61K 31/19; A61K 33/18; A61K 47/18; A61K 47/20; A61K 47/24
See application file for complete search history.

(56) References Cited

U.S. PATENT DOCUMENTS

| | | | |
|---|---|---|---|
| 3,728,449 A * | 4/1973 | Cantor et al. ............... 424/671 |
| 4,401,651 A | 8/1983 | Knutson | |
| 4,597,975 A | 7/1986 | Woodward et al. | |
| 4,755,378 A * | 7/1988 | Buxton et al. ............... 424/78.07 |
| 4,844,898 A | 7/1989 | Komori et al. | |
| 5,256,701 A | 10/1993 | Tamura et al. | |
| 5,558,881 A | 9/1996 | Beck | |
| 5,663,208 A | 9/1997 | Martin | |
| 5,665,776 A | 9/1997 | Yu et al. | |
| 5,753,270 A | 5/1998 | Beauchamp et al. | |
| 5,843,408 A | 12/1998 | Masayuki | |
| 5,897,872 A | 4/1999 | Picciano | |
| 5,908,619 A | 6/1999 | Scholz | |
| 5,951,993 A | 9/1999 | Scholz et al. | |
| 6,559,189 B2 | 5/2003 | Baker, Jr. et al. | |
| 6,582,711 B1 | 6/2003 | Asmus et al. | |
| 6,635,676 B2 | 10/2003 | Baker, Jr. et al. | |
| 6,696,041 B2 | 2/2004 | Hansen | |
| 6,838,078 B2 | 1/2005 | Wang et al. | |
| 6,846,846 B2 | 1/2005 | Modak et al. | |
| 7,060,253 B1 | 6/2006 | Mundschenk | |
| 7,147,873 B2 | 12/2006 | Scholz et al. | |
| 2002/0086039 A1 | 7/2002 | Lee et al. | |
| 2002/0098154 A1 | 7/2002 | Dyer | |
| 2002/0119205 A1 | 8/2002 | Hassan | |
| 2003/0180380 A1 | 9/2003 | Hansen | |
| 2003/0228376 A1 | 12/2003 | Mody et al. | |
| 2005/0053593 A1 * | 3/2005 | Wang et al. ................. 424/94.1 |
| 2005/0089539 A1 | 4/2005 | Scholz et al. | |
| 2005/0191270 A1 | 9/2005 | Gruening et al. | |
| 2006/0051384 A1 | 3/2006 | Scholz et al. | |
| 2006/0052452 A1 | 3/2006 | Scholz | |
| 2007/0048345 A1 * | 3/2007 | Huang et al. ................ 424/405 |

FOREIGN PATENT DOCUMENTS

| | | |
|---|---|---|
| CN | 1323584 | 11/2001 |
| DE | 103 60 847 A1 | 7/2005 |
| EP | 0 213 717 | 3/1987 |
| EP | 0 659 401 | 6/1995 |
| GB | 2 276 546 | 10/1994 |
| JP | 62-045528 | 2/1987 |
| JP | 07-330619 | 12/1995 |
| JP | 2000-507217 | 6/2000 |
| JP | 2005-515235 | 5/2005 |
| RU | 2 220 710 | 1/2004 |
| WO | WO 88/04168 A1 * | 6/1988 |
| WO | WO 1997/31643 | 9/1997 |
| WO | WO 02/094179 | 1/2002 |
| WO | WO 2003/061389 | 7/2003 |

OTHER PUBLICATIONS

P. R. R Nandy, U. S. Dwivedi, N. Vyas, M. Prasad, B. Dutta, and P. B. Singh, "Povidone Iodine and Dextrose Solution Combination Sclerotherapy in Chyluria", Urology, 64: 1107-1110, 2004.*
Elizabeth T. Houang, 0. J. A. Gilmore, Clare Reid, and Elizabeth J. Shaw, "Absence of bacterial resistance to povidone iodine", Journal of Clinical Pathology, 1976, 29, 752-755.*
Kisan R. Jadhav, Manoj N. Gambhire, Ishaque M. Shaikh, Vilarsrao J. Kadam and Sambjahi S. Pisal, "Nasal Drug Delivery System-Factors Affecting and Applications", Current Drug Therapy, 2007, 2, 27-38.*
ASTM E1173-93 Standard Test Method of a Evaluation of a Preoperative, Precatheterization, or Preinjection Skin Preparations, ASTM International, West Conshohocken, PA, 2001, https://doi.org/10.1520/E1173-93.*
ASTM E 1173-93, "Standard Test Method for Evaluation of a Pre-Operative Skin Preparation," *Annual Book of ASTM Standards*, Apr. 1993, pp. 830-832.

(Continued)

*Primary Examiner* — John Pak
*Assistant Examiner* — Nathan W Schlientz
(74) *Attorney, Agent, or Firm* — 3M Innovative Properties Company; Carlos M. Téllez

(57) ABSTRACT

The present invention relates to compositions that contain iodine intended primarily for tissue antisepsis, particularly skin antisepsis.

46 Claims, No Drawings

(56) References Cited

OTHER PUBLICATIONS

ASTM D 3278-96, "Standard Test Methods for Flash Point of Liquids by Small Scale Closed-Cup Apparatus," *Annual Book of ASTM Standards*, Nov. 2004, pp. 1-8.

ASTM D 3574-95, "Standard Test Methods for Flexible Cellular Materials—Slab, Bonded, and Molded Urethane Foams," *Annual Book of ASTM Standards*, May 1995, pp. 161-178.

Bailly et al., "Effect of nasal decontamination by Betadine® ointment on the incidence of colonization of central venous catheters by coagulase negative *Staphylococci* in intensive care units," *Med Mal Infect*, 1999;29:385-394. (English Abstract).

"Betadine Antiseptic Ointment 80g" catalogue sheet. [online]. Westons Internet Home Health. [retrieved on Oct. 2, 2007]. Retrieved from the Internet:<URL:http://www.westonshealth.co.uk/acatalog/info_BET193H.html>; 1 pg.

"Betadine Ointment" datasheet [online]. Molnlycke Health Care, Two Omega Drive, Irlam , Manchester M44 5BJ, United Kingdom, Sep. 20, 2005. [retrieved on Oct. 2, 2007]. Retrieved from the Internet:<URL:http:emc.medicines.org.uk/emc/assets/c/html/DisplayDoc.asp?DocumentID=1955>; 6 pgs.

Gottardi, W.; Chapter 8 entitled "Iodine and Iodine Compounds," in *Disinfection, Sterilization, and Preservation*, by Seymour S. Block; 4$^{th}$ edition, Lea & Febiger, Philadelphia, PA. 1991, cover page, publication page and table of contents; pp. 152-166.

Fong, I.W., "Prevention of haemodialysis and peritoneal dialysis catheter related infection by topical povidone-iodine," *Postgraduate Medical Journal*, 1993;69(Suppl 3): S15-S17.

Fujihara et al., "The Effectiveness of Nasal Nebulizer Therapy with Cefmenoxime Hydrochloride and Nasal Drops of Povidone Iodine for Acute Rhinosinusitis in Children," *Practica Oto-Rhino-Laryngologica*, 2004;97(7):599-604. (English Abstract).

Gosepath et al., "Topical Antibiotic, Antifungal, and Antiseptic Solutions Decrease Ciliary Activity in Nasal Respiratory Cells," *American Journal of Rhinology*, Jan.-Feb. 2002;vol. 16, No. 1 pp. 25-31.

Goodard et al., "Novel gelling structures based on polymer/surfactant systems," *J. Soc. Cosmet. Chem.*, 42; Jan./Feb. 1991; pp. 19-34.

Hill et al., "Elimination of Nasal Carriage of *S. aureus* with 5% Povidone-Iodine Cream: a Double-Blind Placebo-Controlled Trial," *Abstracts of the Interscience Conference on Antimicrobial Agents and Chemotherapy*, 2000;40:483.

Hill et al., "The in-vitro activity of povidone-iodine cream against *Staphylococus aureus* and its bioavailability in nasal secretions," *Journal of Hospital Infection*, (2000) 45; pp. 198-205.

Hill et al., "In-vitro Activity of Betadine Cream Against Mupirocin-Sensitive and—Resistant *Staphylococcus aureus*," Abstract. p. 9.2.10.: 1 pg.

Kawana and Kudo, "A Trial of Povidone-iodine (PVP-I) Nasal Inhalation and Gargling to Remove Potentially Pathogenic Bacteria Colonized in the Pharynx," *Journal of Japanese Association for Infectious Diseases*, May 1999;73(5):429-436 (English Abstract).

Kaye E.T., "Topical Antibacterial Agents," *Infectious Disease Clinics of North America*, Jun. 2000; vol. 14; No. 2; pp. 321-339.

Lio, et al., "Topical antibacterial agents," *Infectious Disease Clinics of North America*, 18 (2004) pp. 717-733.

Masano et al., "Efficacy of intranasal application of povidone-iodine cream in eradicating nasal methicillin-resistant *Staphylococcus aureus* in neonatal intensive care unit (NICU) staff," *Postgraduate Medical Journal*, 1993; 69 (Suppl 3): S122-S125.

Nobukuni et al., "The Influence of Long-Term Treatment with Povidone-Iodine on Thyroid Function," *Dermatology*, 1997; 195 (Suppl 2) pp. 69-72.

Ogata et al., "Gargling with povidone-iodine reduces the transport of bacteria during oral intubation," *Canadian Journal of Anesthesia* 2004; 51(9); pp. 932-936.

Reimer et al., "Antimicrobial Effectiveness of Povidone-Iodine and Consequences for New Application Areas," *Dermatology*, 2002; 204(Supp 1);pp. 114-120.

Rombaux et al., "The role of nasal cavity disinfection in the bacteriology of chronic sinusitis," *Rhinology*, 43, pp. 125-129, 2005.

Rudolph et al., "Efficacy and Local Tolerability of Povidone Iodine and Octenidine Hydrochloride Solution for the Antiseptic Preparation of the Orificium Urethrae," *Infection*, 27 (1999) No. 2; pp. 108-113.

Seipp and Hehl, "Multiresistante *Staphylococcus aureus*," *Hyg Med*, vol. 22, No. 2; 1997; pp. 61-72.

Cajori, F.A., "The use of Iodine in the determination of Glucose, Fructose, Sucrose, and Maltose," *Determination of Sugars*, Department of Chemistry, Stanford University, California, Oct. 22, 1922: 617-627.

Gottardi, "Iodine and Iodine Compounds," Chapter 8, *Disinfection, Sterilization, and Preservation*, 4$^{th}$ Edition, Lea & Febiger, Seymour S. Block, Ph.D., University of Florida, 1991: pp. 152, 153, 155, and 156.

O'Connor et al., "Phenolic Compounds," Chapter 12, *Disinfection, Sterilization, and Preservation*, 4$^{th}$ Edition, Lea & Febiger, Seymour S. Block, Ph.D., University of Florida, 1991: pp. 204, 215, and 216.

Merianos, John, "Quaternary Ammonium Antimicrobial Compounds," Chapter 13, *Disinfection, Sterilization, and Preservation*, 4$^{th}$ Edition, Lea & Febiger, Seymour S. Block, Ph.D., University of Florida, 1991: pp. 225, 250, 251.

Denton, Graham W., "Chlorhexidine," Chapter 16, *Disinfection, Sterilization, and Preservation*, 4$^{th}$ Edition, Lea & Febiger, Seymour S. Block, Ph.D., University of Florida, 1991: pp. 274-276.

Najafi, R.B. et al.; "Formulation and Chemical Evaluation of Povidone-Iodine Ophthalmic Drop"; Iranian Journal of Pharmaceutical Research; vol. 2; 2003; pp. 157-160.

* cited by examiner

LIQUID ANTISEPTIC COMPOSITIONS CONTAINING IODINE AND A SUGAR AND/OR SUGAR ALCOHOL

CROSS REFERENCE TO RELATED APPLICATIONS

This application claims the benefit of U.S. Provisional Patent Application Ser. No. 61/018,109, filed Dec. 31, 2007, which is incorporated herein by reference.

BACKGROUND

It is a standard practice in the industrialized world to disinfect the skin prior to any invasive procedure such as surgery, catheterization, or needle puncture to reduce the risk of infection. Decontamination of the oral cavity and nasal cavity also has been suggested to reduce the incidence of infection in cardiac surgery and/or to reduce spread of Methicillin Resistant *Staphylococcus aureus* (MRSA) in healthcare facilities. These products are often referred to as skin preps, nasal preps, oral preps, or simply "preps". It is particularly advantageous to customers to have a single product that can be used on both intact skin and mucosal tissue (e.g., vaginal, oral, nasal, and ocular tissue). Other sensitive tissues that antimicrobial products have been used on include acute and chronic wounds as well as burns. For all of these topical antiseptics it is desirable to achieve a very rapid microbial reduction so that the clinician can get on with the intended procedure.

Recently, there have been several alcohol-based antiseptics on the market for both presurgical and precatherization antisepsis. These products, while good rapid acting antiseptics due to the high alcohol content (e.g., typically at least 60 percent by weight (wt-%)), are only suitable for use on intact skin and are not suitable for use on sensitive tissues such as mucosal tissue, wounds, or burn tissue. High alcohol concentrations can be extremely irritating to these tissues.

More recently there has been a number of papers published showing that patients who carry *Staphylococcus aureus* (SA) in their nose at the time of surgery are at much greater risk of acquiring a surgical site infection. Thus, what is needed is a presurgical prep that also can be used in the nose and particularly in the anterior nares. The only product routinely used for this purpose in the United States is Bactroban Nasal. This product contains the antibiotic mupirocin. This antibiotic is effective but has been found to generate bacterial resistance quite easily.

It is well known that none of the commercially available skin antiseptics kill all of the bacteria on the skin. For this reason, recent products have incorporated film-forming polymers that resist wash-off during surgery or exposure to fluids. Some of these products also require an organic remover solution or lotion to get the prep off the skin. This is inconvenient for the clinician and requires significant extra time.

Furthermore, many current preps have very low viscosity and thus are messy to apply to body cavities such as the vagina and nose since they spill out. Finally, many of these preps do not kill bacteria very rapidly and/or have an objectionable odor and/or taste. Povidone iodine preps (such as BETADINE 10% povidone-iodine solution from Purdue Frederick, Norwalk, Conn.) are widely recognized for their efficacy on skin and in the vaginal cavity, and for lack of bacterial resistance, but these preps have very low viscosity and do not kill as rapidly as desired. Furthermore, preps such as BETADINE have an unpleasant odor and taste.

Thus, there is still a need for tissue antiseptic compositions.

SUMMARY

The present invention relates to compositions that contain at least one antimicrobial agent intended primarily for tissue antisepsis. Such compositions are particularly useful in prepping the skin and mucosal tissue (including oral tissue, nasal passages including the anterior nares, esophagus, and vagina) prior to an invasive procedure being performed on the subject.

In one embodiment, the present invention provides a tissue antiseptic composition that includes: an antimicrobial agent selected from the group consisting of iodine ($I_2$), an iodophor, and a combination thereof, wherein the antimicrobial agent is present in a sufficient concentration to provide an available iodine concentration of 0.1 wt-% to 2 wt-%; a monosaccharide, a sugar alcohol, or a combination thereof; and a vehicle that is a liquid at 23° C.; wherein the composition is a liquid at 23° C.

In another embodiment, the present invention provides a tissue antiseptic composition that includes: an antimicrobial agent selected from the group consisting of iodine ($I_2$), an iodophor, and a combination thereof, wherein the antimicrobial agent is present in a sufficient concentration to provide an available iodine concentration of 0.1 wt-% to 2 wt-%; a monosaccharide, a sugar alcohol, or a combination thereof; a surfactant; and a vehicle comprising a major amount of a water-soluble glycol humectant (preferably, a water-soluble polyalkylene glycol); wherein the composition is a liquid at 23° C.

In yet another embodiment, the present invention provides a tissue antiseptic composition that includes: an antimicrobial agent selected from the group consisting of iodine ($I_2$), an iodophor, and a combination thereof, wherein the antimicrobial agent is present in a sufficient concentration to provide an available iodine concentration of 0.1 wt-% to 2 wt-%; a monosaccharide, a sugar alcohol, or a combination thereof; and a vehicle; wherein the composition has a viscosity of greater than 1000 cps; and wherein the composition is a liquid at 23° C.

The present invention also provides methods.

In one embodiment, there is provided a method of decolonizing the nasal passages of a subject. The method involves applying a composition of the present invention to the nasal passages of the subject.

In yet another embodiment, there is provided a method of disinfecting the tissue of a subject. The method involves applying a composition of the present invention to the tissue of the subject.

The terms "tissue antiseptic composition," "antiseptic composition," "composition," "skin prep," and "prep" herein refer to a composition that is active against (i.e., effective at killing and/or deactivating) at least one bacterium on skin and/or mucosal tissue. The term "liquid" when referring to such compositions (or vehicles contained therein) herein mean that the compositions (or vehicles) are liquids at 23° C., which flow to form the shape of the container in which they are placed (except for the free surface formed at the top). Some liquids of the present invention may be relatively viscous. Such compositions when placed in a centrifuge tube and placed a low speed of approximately 50×g will conform to the shape of the centrifuge tube (except for the free surface formed at the top). Hence, such compositions are not in the form of lozenges or bars (e.g., bars of soap). Furthermore, preferred liquid compositions described herein are "use" compositions. That is, they are in their as-delivered state and are not concentrated compositions.

The term "sugar alcohol" is understood to mean a monosaccharide or a disaccharide in which the aldehyde group of the first carbon atom is reduced to a primary alcohol. Preferred sugar alcohols are alcohols of a monosaccharide. The term "alcohol of a monosaccharide" is understood to mean a monosaccharide in which the aldehyde group of the first carbon atom is reduced to a primary alcohol.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a composition that comprises "a" monosaccharide can be interpreted to mean that the composition includes "one or more" monosaccharides. Similarly, a composition comprising "a" surfactant can be interpreted to mean that the composition includes "one or more" surfactants.

As used herein, the term "or" is generally employed in its sense including "and/or" unless the content clearly dictates otherwise.

The term "and/or" means one or all of the listed elements or a combination of any two or more of the listed elements (e.g., killing and/or inactivating a bacterium means inactivating, killing, or both inactivating and killing the bacterium).

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The present invention provides tissue antiseptic compositions that include iodine (preferably provided in the form of an iodophor) and a monosaccharide and/or a sugar alcohol (preferably, an alcohol of a monosaccharide).

The compositions described herein are liquids at 23° C. The liquids generally have viscosity values of 1-500,000 cps as determined as described in the Brookfield Viscosity Test in the Example Section.

Antiseptic compositions of the present invention have one or more of the following properties: relatively high levels of bacterial kill; relatively rapid speed and/or length of bactericidal activity; not likely to generate bacterial resistance; capable of releasing iodine over a period of time; suitable for use on sensitive tissues such as mucosal tissue including vaginal, oral, esophageal and nasal tissue; relatively non-irritating to a majority of users; acceptable odor; acceptable taste in the event some of the composition is deliberately used in the oral or esophageal cavity or if the composition is placed in the nose and migrates up the nasal passages and down the throat; good adhesion to the skin and/or mucosal tissue when both wet and dry; sufficiently high viscosity to provide substantivity to mucosal tissue such that the residence time in the nose or other mucosal tissue (e.g., oral, vaginal, or esophageal) is increased over a non-thickened formulation; preferably good adhesion of pressure sensitive adhesive (PSA) coated products such as incise drapes, tapes, wound dressings, and the like, over the dried prep on skin (preferably, for long periods of time, e.g., hours to days); resist lift off of PSA-coated products over the dried prep on skin while under stress as typically occurs during retraction in surgery; can be removed relatively easily, preferably without the need for organic solvent-based removers.

Preferred antiseptic compositions of the present invention possess many or all of the above-mentioned characteristics. Significantly, they provide rapid broad spectrum microbial kill, with very little or no chance of bacterial resistance, are well tolerated on mucosal tissue, and have an acceptable odor and taste. Furthermore, they are gentle to tissue and can be removed with a water-soaked fabric, such as a towel or simple gauze.

Furthermore, preferred compositions of the present invention are very stable and can survive prolonged exposure to elevated temperatures, e.g., 50° C. and even as high as 60° C., for prolonged periods of time, e.g., for often greater than 7 days. The most stable samples show no visible changes, such as changes in color, turbidity, and the like when returned to room temperature (23 C) for at least 12 hours. Also, preferred compositions of the present invention are very stable upon exposure to low temperatures, e.g., 4° C., and even during repeated freeze/thaw cycles, e.g., 2 or more cycles.

Preferred compositions of the present invention are also generally substantive. More preferred compositions of the present invention are substantive while in moist environments, such as the nose, anterior nares, and vaginal vault and remain on any of these tissues for longer periods of time than typical antiseptics such as BETADINE 10% povidone-iodine solution (Purdue Frederick, Norwalk, Conn.).

A "substantive" composition is one that when placed in the anterior nares has visible iodine still present 30 minutes (min) after instillation of 0.25 milliliter (mL) with a cotton bud and gently massaging the nostrils for 5 seconds to ensure an even distribution as long (as the patient does not discharge or deliberately or inadvertently wipe the product away). Preferred substantive compositions remain present in the anterior nares for 45 min, and more preferably for 60 min, post instillation. This is conveniently determined by dabbing the inside of the anterior nares with a white tissue such as a KLEENEX tissue or by imparting color to the composition (e.g., inclusion of a small amount of a dye or a colored active such as povidone-iodine in sufficient concentration that a relatively dark color results on the skin that can be easily seen as present or not).

Many of the compositions of this invention are also "skin substantive" and thus a dried composition resists removal from skin for at least 15 seconds when tested as described in the "Substantivity Test" described in U.S. Pat. No. 7,147,873. Preferably, for use on skin, the compositions are even more substantive and resist being removed under the same conditions for at least 30 seconds, more preferably at least 45 seconds, and most preferably at least 60 seconds. This is conveniently determined by imparting color to the composition (e.g., inclusion of a small amount of a dye or a colored active such as povidone-iodine in sufficient concentration that a relatively dark color results on the skin that can be easily seen as present or not).

The dried films of preferred antiseptic compositions of the present invention that include a film-forming polymer are generally flexible and durable. That is, they do not crack or flake off as brittle films might do. Significantly, film-forming polymers contribute to achieving a delicate balance between low tack and flexibility.

Although antiseptic compositions of the present invention can be of a wide variety of viscosities, preferred compositions possess viscosities that ensure the formulations go on easily and form a substantive film, particularly on wet tissue (such as mucosal tissue). Preferably, the Brookfield viscosity of a composition is greater than 100 Centipoise (cps), more preferably greater than 500 cps, even more preferably greater than 1000 cps, even more preferably greater than 2000 cps, and most preferably greater than 5000 cps. Certain skin antiseptic compositions of the present invention resist removal particularly well after they are dry. These compositions generally have lower viscosity (e.g., less than 1000 cps), and preferably greater than 10 cps. Viscosities herein are measured at 23° C. using a Brookfield RVT ROTO-VISCO viscometer and the procedure described in the Examples Section.

A relatively low viscosity ensures that the composition can be painted on the skin or mucosal tissue with little effort in a uniform thin film that may dry rapidly. Thus, the viscosities of preferred compositions for use on intact skin of this invention are no greater than 500,000 cps, preferably no greater than 200,000 cps, more preferably no greater than 50,000 cps, still more preferably no greater than 10,000 cps, and most preferably no greater than 5,000 cps. For use on wound or musocal tissue, such as in the nasal cavity or vagina, the viscosity is preferably relatively high to minimize drainage and mess. On wound and mucosal tissue the composition may not dry in use. Thus, the high viscosity helps to maintain the composition at the application site for extended periods of time to improve microbial kill.

A particularly important property of antiseptic compositions of the present invention for use on skin, wound, or mucosal tissue is the ability to reduce the bacterial load on tissue, particularly skin (e.g., to kill the natural skin flora), rapidly. Preferably, compositions of the present invention are capable of reducing normal skin flora by at least 1 log (10-fold), more preferably by at least 1.5 log, and most preferably by at least 2 logs (100-fold), in 2 minutes on a dry human skin site (typically, skin on an abdomen or back) using ASTM testing method E1173-93 and a 30-second scrub with gauze soaked in the composition using moderate pressure.

This surprising rapid and high antimicrobial activity is provided through the use of iodine, preferably delivered as an iodophor to reduce irritation potential, as the active antimicrobial agent, in combination with a monosaccharide and/or a sugar alcohol. Preferred compositions further comprise one or more hydroxycarboxylic acid buffers in particularly high use concentrations. The monosaccharides and/or sugar alcohols, and hydroxycarboxylic acid buffers in the compositions contribute significantly to such good bacterial kill. By comparison, a composition of the present invention reduces normal skin flora by at least 0.5 log more than the same composition without the hydroxycarboxylic acid buffer, monosaccharide and/or sugar alcohol present. This "same" composition includes additional water instead of the monosaccharide, sugar alcohol, or hydroxycarboxylic acid buffer and would be adjusted to the same pH as the composition with these components using a mineral acid or base, such as hydrochloric acid or sodium hydroxide, that does not compromise the stability of the composition. Surprisingly, the placebo compositions (i.e., compositions without an antimicrobial agent but still including the monosaccharide, sugar alcohol, and/or hydroxycarboxylic acid buffer) are relatively inactive. By comparison, a composition of the present invention reduces normal skin flora by at least 0.5 log more than the same composition without the iodine or iodophor present when tested on a dry human skin site (e.g., back or abdomen) according to ASTM testing method E1173-93 measured 2 minutes after completion of a 30-second scrub with gauze soaked in the composition using moderate pressure.

Generally, antiseptic compositions are applied to the tissue, typically skin, and allowed to dry and remain in place for at least 2 minutes, and often for several hours to days. Significantly, many of the compositions of the present invention maintain very low bacterial counts on the tissue, typically skin, for long periods of time, e.g., often up to 6 hours, and even up to 24 hours.

Antimicrobial Agents

A preferred active antimicrobial agent is elemental iodine ($I_2$), which can be provided in the form of an iodophor. As in most iodine-containing patient preps, other iodine-containing species may be present in addition to iodine. Such species include, for example, hypoiodous acid (HOI), iodide ($I^-$), triiodide ($I_3^-$), iodate ($IO_3^-$), and the like. It is widely recognized that elemental iodine is the most active antimicrobial species. See, for example, Disinfection, Sterilization, and Preservation by Seymour S. Block, 4.sup.th edition, Chapter 8 "Iodine and Iodine Compounds," Lea & Febiger, Philadelphia, Pa., 1991. Minor amounts of $Br^-$ and or $Cl^-$ also may be present.

In most commercially available iodine disinfectants, in order to prevent rapid reduction of iodine to iodide the solutions are typically buffered to be slightly acidic (e.g., 6 or less, and often 2 to 6). The acidity is typically desired to maintain stability in the iodine solutions and to suppress conversion to other iodine species that are less germicidal. For example, commercial skin preps containing iodine generally have pH values in the range of 3 to 5, which favors stability of the molecular iodine species. HOI normally exists in very low levels relative to $I_2$ but has been reported as an effective antimicrobial and may contribute to kill in some compositions. $IO_3^-$ is an effective oxidant only at pH values less than 4, where significant amounts of $HIO_3$ can exist.

As further background for understanding and practicing the present invention, elemental iodine is only slightly soluble in water (0.03 wt-% at 25° C.). Alkali metal iodides, which combine with iodine to form triiodide ($I^-$), increase that solubility. Molecular iodine, however, can be very irritating at higher concentrations. For example, Lugol's solution (5% elemental iodine and 10% potassium iodide) and tincture of iodine (45% aqueous ethanol with 2% elemental iodine and 2.4% sodium iodide) have both been well documented to be quite irritating to the skin.

Many references have described the preparation of "iodophors," which are complexes of elemental iodine or triiodide with certain carriers. These iodophors function to not only increase the iodine solubility but to reduce the level of free molecular iodine in solution and to provide a type of sustained release reservoir of elemental iodine. Iodophors are known using carriers of polymers such as polyvinylpyrrolidone, copolymers of N-vinyl lactams with other unsaturated monomers such as, but not limited to, acrylates and acrylamides, various polyether glycols including polyether-containing surfactants such as nonylphenolethoxylates and the like, polyvinyl alcohols, polycarboxylic acids such as polyacrylic acid, polyacrylamides, polysaccharides such as dextrose, and the like, and combinations thereof. A preferred group of iodophors include polymers such as a polyvinylpyrrolidone (PVP), a copolymer of N-vinyl lactam, a polyether glycol (PEG), a polyvinyl alcohol, a polyacrylamide, a polysaccharide, and combinations thereof. Also reported in U.S. Pat. No. 4,597,975 (Woodward et al.) are protonated amine oxide surfactant-triiodide complexes that are also suitable iodophors for use in the present invention. Various combinations of iodophors can be used in the compositions of the present invention.

A preferred iodophor is povidone-iodine. A particularly preferred iodophor can be obtained commercially as povidone-iodine USP, which is believed to be a complex of K30 polyvinylpyrrolidone, iodine, and iodide wherein the available iodine is present at 9 wt-% to 12 wt-%.

Preferably, the iodophor is present in the use compositions at a concentration of at least 1 percent by weight (wt-%), preferably at least 2.5 wt-%, and more preferably at least 4 wt-%, and most preferably at least 5 wt-%, based on the total weight of the antiseptic composition. To prevent the dried composition from becoming excessively water soluble and/or to control irritation, iodine toxicity, and poor taste, the concentration of iodophor in the use composition is preferably present at not more than 15 wt-%, and more preferably not more than 10 wt-%, based on the total weight of the antiseptic composition.

Since iodophors may vary in the amount of available iodine it is usually more convenient to describe the concentration in terms of the available iodine level. In the present invention, whether from iodine or an iodophor or a combination thereof, the available iodine concentration is preferably at least 0.1 wt %, more preferably at least 0.2 wt-%, even more preferably at least 0.25 wt-%, and even more preferably at least 0.4 wt-%, based on the total weight of the antiseptic composition. Most preferably, the compositions contain at least 0.50 wt-% available iodine, based on the total weight of the antiseptic composition. Concentrations of available iodine below 0.1 wt-% may not be sufficiently bactericidal. The available iodine is preferably present at not more than 2 wt-%, more preferably no more than 1.5 wt-%, and even more preferably not more than 1 wt-%, based on the total weight of the antiseptic composition. Concentrations of available iodine above 2 wt-% may be too irritating to wound and mucosal tissue and skin. The available iodine for most compositions may be determined by following the method in the United States Pharmacopeia Official Monographs for Povidone-Iodine, Assay for Available Iodine. Certain formulations may contain components that can interact with the method such as other anionic species. For this reason, the proper standards must be run to ensure accuracy, and solvent systems or reagents may need to be changed to ensure accuracy. One skilled in the art would appreciate these considerations.

Monosaccharides and Sugar Alcohols

The monosaccharides used herein have the chemical formula $(CH_2O)_{n+m}$ with the chemical structure $H(CHOH)_n C=O(CHOH)_m H$. If n or m is zero, it is an aldehyde and is termed an aldose, otherwise it is a ketone and is termed a ketose. Monosaccharides contain either a ketone or aldehyde functional group, and hydroxyl groups on most or all of the non-carbonyl carbon atoms. The monosaccarides found most useful are 5 and 6 carbon atom (n+m=5 or 6) compounds. They may be found in the D or L form or a combination thereof. The most preferred monosaccharides are xylose, xylulose, lyxose, mannose, maltose, sorbose, erythrose, glucose (dextrose), fructose, galactose, and ribose The term "sugar alcohol" is understood to mean a monosaccharide or a disaccharide in which the aldehyde group of the first carbon atom is reduced to a primary alcohol. They include the following preferred sugar alcohols: xylitol, sorbitol, mannitol, maltitol, erythritol, lactitol and arabitol or combinations thereof. More preferred sugar alcohols are those derived from monosaccharides (i.e., alcohols of a monosaccharide) including xylitol, mannitol, or combinations thereof. A particularly preferred sugar alcohol is xylitol. As used herein, the term "alcohol of a monosaccharide" is understood to mean a monosaccharide in which the aldehyde group of the first carbon atom is reduced to a primary alcohol.

These monosaccharides and/or sugar alcohols surprisingly have been found to increase the efficacy (speed and/or extent of bacterial kill) of iodine containing compositions.

The monosaccharides and/or sugar alcohols are preferably present in a concentration of at least 0.25 wt-%, more preferably at least 0.5 wt-%, even more preferably at least 1 wt-%, even more preferably at least 2 wt-%, even more preferably at least 4 wt-%, and even more preferably at least 5 wt-%, based on the total weight of the composition. The concentration is typically adjusted to ensure improved antimicrobial performance and/or to improve the taste of the composition if it is applied to the oral cavity, esophageal cavity, nasal passages, or anterior nares. The upper limit may be determined by the solubility limit of the monosaccharide and/or sugar alcohol. In preferred compositions the monosaccharide and/or sugar alcohol is completely soluble with no solid dispersed therein. Such formulations are easier to maintain physical stability, i.e., to prevent settling and non-uniformity. Stability should be examined 2-4 weeks after manufacture when stored at room temperature. Preferred formulations do not exhibit any solid monosaccharide and/or sugar alcohol after standing. For example, it has been found that in PEG 400 xylitol is initially in solution when heated to 70° C. Upon standing for 2 weeks, however, some of the compositions showed separation of solid xylitol. Addition of 5-20 wt-% water was found to keep the xylitol stable in solution (depending on the amount of xylitol used).

Hydroxycarboxylic Acid Buffers

The compositions of the present invention are preferably buffered to prevent pH drift during storage. For example, it is well known that for iodine-containing systems it is desired to maintain the pH at generally 2 to 6, and preferably at 3 to 5. As the pH is raised above 6, the iodine can be rapidly converted to iodide, thus inactivating the antimicrobial effectiveness, if such is desired. Much below a pH of 2 and the composition may become irritating. In the compositions of the present invention, the pH is preferably adjusted to 3.0 to 4.5, and more preferably to 3.5 to 4.2.

While conventional compositions have included a variety of organic and inorganic buffers at concentrations of 0.1 wt-% to 2 wt-%. Compositions of the present invention include certain hydroxycarboxylic acid buffers that can be used in much higher buffer concentrations. Preferably, a hydroxycarboxylic acid buffer is present in an amount of greater than 1 wt-%, more preferably greater than 2.5 wt-%, even more preferably greater than 3 wt-%, and even more preferably greater than 5 wt-%, and most preferably greater than 6 wt-%, based on the total weight of the antiseptic composition.

Surprisingly, these compositions (i.e., with a pH preferably adjusted to 3.0 to 4.5, and more preferably to 3.5 to 4.2, and a relatively high hydroxycarboxylic acid buffer concentration—greater than 2.5 wt-%, and more preferably greater than 5 wt-%) are substantially nonirritating to tissue (e.g., skin and mucosal tissue), as indicated by studies conducted by instilling aliquots (of use concentrations) into rabbit eyes. Preferred compositions when tested according to the Rabbit Eye Irritation Test disclosed in U.S. Pat. No. 7,147,873 produce very little, if any, corneal opacity, with substantially complete return to normal (i.e., clear or having a Draize score of zero) in no greater than 96 hours, and preferably no greater than 72 hours. This indicates that the compositions would be very gentle for use on skin and mucosal tissue. This is very surprising since previous reports have indicated that high levels of alpha-hydroxy acids at an acidic pH can be irritating to the skin.

This level of buffer is particularly desirable for antiseptic compositions that include povidone-iodine (particularly povidone-iodine USP) as the antimicrobial agent. In these systems the level of rapid microbial kill increases significantly and for some systems in a linear fashion with the molar concentration of the hydroxycarboxylic acid.

Preferred hydroxycarboxylic acid buffers include one or more compounds disclosed in U.S. Pat. No. 7,147,873 and are represented by the formula: $R^1(CR^2OH)_n(CH_2)_mCOOH$ wherein: $R^1$ and $R^2$ are each independently H or a (C1-C8) alkyl group (saturated straight, branched, or cyclic group), a (C6-C12)aryl, or a (C6-C12)aralkyl or alkaryl group (saturated straight, branched, or cyclic alkyl group), wherein $R^1$ and $R^2$ may be optionally substituted with one or more carboxylic acid groups; m=0 or 1; and n=1-3, preferably, n=1-2.

It is particularly desirable that the buffers and other excipients that contain hydrocarbon groups are saturated or contain low levels of unsaturation to prevent iodine addition, which may deplete the iodine in the composition and/or produce toxic species. Preferably, the level of unsaturation in the composition is no greater than 50 milliequivalents per liter (meq/L), more preferably, no greater than 5 meq/L, and most preferably, no greater than 0.5 meq/L unsaturation.

The hydroxycarboxylic acid buffers of the present invention include preferably beta- and alpha-hydroxy acids (BHAs, AHAs, respectively, collectively referred to as hydroxy acids (HAs)), salts thereof, lactones thereof, and/or derivatives thereof (preferably, alpha-hydroxy acids are used). These may include mono-, di-, and tri-functional carboxylic acids. Particularly preferred are HAs having 1 or 2 hydroxyl groups and 1 or 2 carboxylic acid groups. Suitable HAs include, but are not limited to, lactic acid, malic acid, citric acid, 2-hydroxybutanoic acid, 3-hydroxybutanoic acid, mandelic acid, gluconic acid, tartaric acid, salicylic acid, as well as derivatives thereof (e.g., compounds substituted with hydroxyls, phenyl groups, hydroxyphenyl groups, alkyl groups, halogens, as well as combinations thereof). Preferred HAs include lactic acid, malic acid, and citric acid. These acids may be in D, L, or DL form and may be present as free acid, lactone, or salts thereof. Other suitable HAs are described in U.S. Pat. No. 5,665,776 (Yu et al.). The preferred HAs for use with iodine, and in particular with povidone-iodine, are lactic and malic acid. Various combinations of hydroxycarboxylic acids can be used if desired.

A hydroxycarboxylic acid buffer is preferably present in a molar concentration of at least 0.3 molar, more preferably at least 0.45 molar, and most preferably at least 0.6 molar. For formulations where very rapid microbial kill on skin is desired the hydroxycarboxylic acid concentration is in excess of 0.7 molar.

Optional Surfactants

For effective kill on skin and mucosal tissue the compositions of the present invention preferably include one or more surfactants. Necessarily, the surfactants must be compatible with the antimicrobial agent, the monosaccharides and/or sugar alcohols, as well as any other optional ingredients, such as a thickener or film-forming polymer. It may be particularly desirable when formulating with a film-forming polymer to include one or more surfactants to enhance solubility and stability of the polymer in the composition. In addition, surfactants help the compositions to wet the skin and ensure a smooth uniform coating. It is particularly desirable to provide a coating (preferably, substantive) that has complete coverage to ensure easy error-free application. On tissues that are hard to visualize, such as most mucosal surfaces, it is desirable to use surfactants to help wetting and to ensure the antimicrobial agent will be distributed by diffusion and or capillary action across the tissue. On skin it is preferred that a thin relatively uniform coating is applied that will dry rapidly. In addition, certain surfactants may increase the antimicrobial activity.

If used, one or more surfactants are generally added to the antiseptic compositions of the present invention in an amount of at least 0.5 wt-%, based on the total weight of the composition. Preferably, one or more surfactants are generally added to the antiseptic compositions of the present invention in an amount of no greater than 12 wt-%, more preferably no greater than 8 wt-%, even more preferably no greater than 6 wt-%, and most preferably no greater than 5 wt-%, based on the total weight of the composition. Too little surfactant may result in an unstable composition (especially upon exposure to elevated temperatures) and/or reduced antimicrobial efficacy on tissue. Too much surfactant can undermine the substantivity of the dried composition on skin. For this reason, the surfactant level is generally chosen as slightly above the minimum level of total surfactant required to ensure stability at 50° C.

Furthermore, it is preferred to use surfactants having low inorganic salt impurities such as sodium chloride, sodium sulfate, etc. Preferably, such salt content should be sufficiently low such that a 20% solution of the surfactant in water has a conductivity of less than 100 micromhos per centimeter (micromhos/cm), more preferably less than 85 micromhos/cm, and most preferably less than 75 micromhos/cm.

The following types of surfactants can be used if desired:

a. Nonionic Surfactants. Particularly useful surfactants are nonionic surfactants. It has been found that polyalkoxylated, and in particular polyethoxylated, nonionic surfactants can stabilize film-forming polymers in aqueous solutions particularly well. In general, useful polyalkoxylated nonionic surfactants preferably have a hydrophile/lipophile balance (HLB) of at least 14, and more preferably at least 16. Useful polyalkoxylated nonionic surfactants preferably have an HLB of no greater than 19. When using combinations of nonionic surfactants a weight average HLB is used to determine the HLB of the nonionic surfactant system. As used herein, the HLB is defined as one-fifth the weight percentage of ethylene oxide segments in the surfactant molecule.

Surfactants of the nonionic type that have been particularly useful include:

1. Polyethylene oxide extended sorbitan monoalkylates (i.e., POLYSORBATES). In particular, a Polysorbate 20 commercially available as NIKKOL TL-10 (from Barret Products) is very effective.
2. Polyalkoxylated alkanols. Surfactants such as those commercially available under the trade designation BRIJ from ICI Specialty Chemicals, Wilmington, Del., having an HLB of at least 14 have proven useful. In particular, BRIJ 78 and BRIJ 700, which are stearyl alcohol ethoxylates having 20 and 100 moles of polyethylene oxide, respectively, have proven very useful. Also useful is a ceteareth 55, which is commercially available under the trade designation PLURAFAC A-39 from BASF Corp., Performance Chemicals Div., Mt. Olive, N.J.
3. Polyalkoxylated alkylphenols. Useful surfactants of this type include polyethoxylated octyl or nonyl phenols having HLB values of at least 14, which are commercially available under the trade designations ICONOL and TRITON, from BASF Corp., Performance Chemicals Div., Mt. Olive, N.J. and Union Carbide Corp., Danbury, Conn., respectively. Examples include TRITON X100 (an octyl phenol having 15 moles of ethylene oxide available from Union Carbide Corp., Danbury, Conn.) and ICONOL NP70 and NP40 (nonyl phenol having 40 and 70 moles of ethylene oxide units, respectively, available from BASF Corp., Performance Chemicals Div., Mt. Olive, N.J.). Sulfated and phosphated derivatives of these surfactants are also useful. Examples of such derivatives include ammonium nonoxynol-4-sulfate, which is commercially available under the trade designation RHODAPEX CO-436 from Rhodia, Dayton, N.J.
4. Polaxamers. Surfactants based on block copolymers of ethylene oxide (EO) and propylene oxide (PO) have been shown to be effective at stabilizing film-forming polymers and provide good wetting. Both EO-PO-EO blocks and PO-EO-PO blocks are expected to work well as long as the HLB is at least 14, and preferably at least 16. Such surfactants are commercially available under the trade designations PLURONIC and TETRONIC from BASF Corp., Performance Chemicals Div., Mt. Olive, N.J. It is noted that the PLURONIC surfactants from BASF have reported HLB values that are calculated differently than described above. In such situation, the HLB values reported by BASF should be used. For example, preferred PLURONIC surfactants are L-64 and F-127, which have HLBs of 15 and 22, respectively. Although the PLURONIC surfactants are quite effective at stabilizing the compositions of the present invention and are quite effective with iodine as the active agent, they may reduce the antimicrobial activity of compositions using povidone-iodine as the active agent.
5. Polyalkoxylated esters. Polyalkoxylated glycols such as ethylene glycol, propylene glycol, glycerol, and the like may be partially or completely esterified, i.e., one or more alcohols may be esterified, with a (C8-C22) alkyl carboxylic acid. Such polyethoxylated esters having an HLB of at least 14, and preferably at least 16, are suitable for use in compositions of the present invention.
6. Alkyl Polyglucosides. Alkyl polyglucosides, such as those described in U.S. Pat. No. 5,951,993 (Scholz et al.), starting at column 9, line 44, are compatible with film-forming polymers and may contribute to polymer stability. Examples include glucopon 425, which has a (C8-C16)alkyl chain length with an average chain length of 10.3 carbons and 1-4 glucose units.

b. Zwitterionic Surfactants. Surfactants of the zwitterionic type include surfactants having tertiary amine groups which may be protonated as well as quaternary amine-containing zwitterionic surfactants. Those that have been particularly useful include:
1. Ammonium Carboxylate Zwitterionics. This class of surfactants can be represented by the following formula:

$$R^3-(C(O)-NH)_a-R^5-N^+(R^4)_2-R^6-COO^-$$

wherein: $a=0$ or $1$; $R^3$ is a (C7-C21)alkyl group (saturated straight, branched, or cyclic group), a (C6-C22) aryl group, or a (C6-C22)aralkyl or alkaryl group (saturated straight, branched, or cyclic alkyl group), wherein $R^3$ may be optionally substituted with one or more N, O, or S atoms, or one or more hydroxyl, carboxyl, amide, or amine groups; $R^4$ is H or a (C1-C8)alkyl group (saturated straight, branched, or cyclic group), wherein $R^4$ may be optionally substituted with one or more N, O, or S atoms, or one or more hydroxyl, carboxyl, amine groups, a (C6-C9)aryl group, or a (C6-C9)aralkyl or alkaryl group; and $R^5$ and $R^6$ are each independently a (C1-C10)alkylene group that may be the same or different and may be optionally substituted with one or more N, O, or S atoms, or one or more hydroxyl or amine groups.

More preferably, in the formula above for ammonium carboxylate zwitterionics, $R^3$ is a (C1-C16)alkyl group, $R^4$ is a (C1-C2)alkyl group preferably substituted with a methyl or benzyl group and most preferably with a methyl group. When $R^4$ is H it is understood that the surfactant at higher pH values could exist as a tertiary amine with a cationic counterion such as Na, K, Li, or a quaternary amine group.

Examples of such zwitterionic surfactants include, but are not limited to: P certain betaines such as cocobetaine and cocamidopropyl betaine (commercially available under the trade designations MACKAM CB-35 and MACKAM L from McIntyre Group Ltd., University Park, Ill.); monoacetates such as sodium lauroamphoacetate; diacetates such as disodium lauroamphoacetate; amino- and alkylamino-propionates such as lauraminopropionic acid (commercially available under the trade designations MACKAM 1L, MACKAM 2L, and MACKAM 151L, respectively, from McIntyre Group Ltd.).

2. Ammonium Sulfonate Zwitterionics. This class of zwitterionic surfactants are often referred to as "sultaines" or "sulfobetaines" and can be represented by the following formula $$R^3-(C(O)-NH)_a-R^5-N^+(R^4)_2-R^6-SO_3^-$$

wherein $R^3$-$R^6$ and "a" are defined as above for ammonium carboxylate zwitterionics. Examples include cocamidopropylhydroxysultaine and lauramidopropylhydroxy sultaine (commercially available as MACKAM 50-SB from McIntyre Group Ltd.).

3. Phospholipid Zwitterionics. These surfactants are characterized as having at lease one anionic phosphate group, one cationic ammonium group (either protonated or quaternary), and at least one alkyl, alkenyl, aralkyl, or aralkenyl group of at least 8 carbon atoms. Many surfactants of this class of surfactants can be represented by the following formula:

$$R^7-OP^-(O)_2O-CH_2CH_2N^+(R^4)_3$$

wherein R⁴ is defined above for ammonium carboxylate zwitterionics and R⁷ is R³ (as defined above for ammonium carboxylate zwitterionics) with the proviso that R⁷ also may comprise multiple R³ groups as would be the case if R⁷ were a glycerol ester derivative as, for example, in phosphatidylcholine. Examples include lecithins, phosphatidylcholine and phosphatidylethanol amine. The so called "reverse phospholipids" which possess a quaternary ammonium group in the chain and a terminal phosphate group are also possible such as those sold by Uniqema/Croda under the tradename Arlasilk Phospholipid CDM (coco PG-dimonium chloride phosphate), Arlasilk Phospholipid EFA (Linoleamidopropyl PG-Dimonium Chloride Phosphate), and the like.

c. Anionic Surfactants. Surfactants of the anionic type that have been particularly useful include:

1. Sulfonates and Sulfates. Suitable anionic surfactants include sulfonates and sulfates such as alkyl sulfates, alkylether sulfates, alkyl sulfonates, alkylether sulfonates, alkylbenzene sulfonates, alkylbenzene ether sulfates, alkylsulfoacetates, secondary alkane sulfonates, secondary alkylsulfates and the like. Many of these can be represented by the formulas:

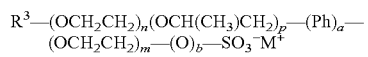

and

wherein: a and b=0 or 1; n, p, m=0-100 (preferably 0-40, and more preferably 0-20); R³ is defined as above for zwitterionics; R⁷ is a (C1-C12)alkyl group (saturated straight, branched, or cyclic group) that may be optionally substituted by N, O, or S atoms or hydroxyl, carboxyl, amide, or amine groups; Ph=phenyl; and M is a cationic counterion such as Na, K, Li, ammonium, a protonated tertiary amine such as triethanolamine or a quaternary ammonium group.

In the formula above, the ethylene oxide groups (i.e., the "n" and "m" groups) and propylene oxide groups (i.e., the "p" groups) can occur in reverse order as well as in a random, sequential, or block arrangement. Preferably for this class, R³ comprises an alkylamide group such as R⁸—C(O)N(CH₃)CH₂CH₂— as well as ester groups such as —OC(O)—CH₂— wherein R⁸ is a (C8-C22)alkyl group (saturated branched, straight, or cyclic group).

Examples include, but are not limited to: alkyl ether sulfonates such as lauryl ether sulfates such as POLYSTEP B12 (n=3-4, M=sodium) and B22 (n=12, M=ammonium) available from Stepan Company, Northfield, Ill. and sodium methyl taurate (available under the trade designation NIKKOL CMT30 from Nikko Chemicals Co., Tokyo, Japan); secondary alkane sulfonates such as Hostapur SAS which is a Sodium (C14-C17)secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo(C12-C16)fatty acid available from Stepan Company under the trade designation ALPHASTE PC-48; alkylsulfoacetates and alkylsulfosuccinates available as sodium laurylsulfoacetate (under the trade designation LANTHANOL LAL) and disodiumlaurethsulfosuccinate (STEPANMILD SL3), both from Stepan Company; alkylsulfates such as ammoniumlauryl sulfate commercially available under the trade designation STEPANOL AM from Stepan Company.

2. Phosphates and Phosphonates. Suitable anionic surfactants also include phosphates such as alkyl phosphates, alkylether phosphates, aralkylphosphates, glycerol ester phosphates, and aralkylether phosphates. Many may be represented by the formula:

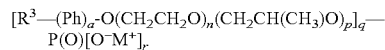

where: Ph, R³, a, n, p, and M are defined above; r is 0-2; and q=1-3; with the proviso that when q=1, r=2, and when q=2, r=1, and when q=3, r=0. As above, the ethylene oxide groups (i.e., the "n" groups) and propylene oxide groups (i.e., the "p" groups) can occur in reverse order as well as in a random, sequential, or block arrangement.

Examples include a mixture of mono-, di- and tri-(alkyltetraglycolether)-o-phosphoric acid esters generally referred to as trilaureth-4-phosphate commercially available under the trade designation HOSTAPHAT 340KL from Clariant Corp., as well as PPG-5 ceteth 10 phosphate available under the trade designation CRODAPHOS SG from Croda Inc., Parsipanny, N.J.

3. Amine Oxides. Suitable anionic surfactants also include amine oxides including alkyl and alkylamidoalkyl-dialkylamine oxides of the following formula:

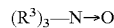

wherein R³ is defined above and each R³ may be the same or different. Optionally, the R³ groups can be joined to form a heterocyclic ring with the nitrogen to form surfactants such as amine oxides of alkyl morpholine, alkyl piperazine, and the like. Preferably two R³ groups are methyl and one R³ group is a (C12-C16) alkyl or alkylamidopropyl group.

Examples of amine oxide surfactants include those commercially available under the trade designations AMMONYX LO, LMDO, and CO, which are lauryldimethylamine oxide, laurylamidopropyldimethylamine oxide, and cetyl amine oxide, all from Stepan Company.

Combinations of various surfactants can be used if desired. For example, nonionic surfactants in combination with certain anionic surfactants or zwitterionic surfactants described above can be used for certain advantage. For example, one preferred surfactant system is based on a combination of a polysorbate and a polyethoxylated alkyl alcohol (POLYSORBATE 20+steareth-100).

Certain preferred zwitterionic surfactants include sultaines, betaines, phospholipids, or combinations thereof. In preferred embodiments, the zwitterionic surfactant is a sultaine, a phospholipids, or a combination thereof.

Certain preferred anionic surfactants include a polyalkoxylate group. These include the sulfonates, sulfates, phosphates, and phosphonates. Various combinations of these can be used if desired.

For certain embodiments, it is desirable to select one or more surfactants that associate or potentially associate with other components in the composition after dry down may be tolerated better. For example, certain anionic surfactants such as methyl-2-sulfoalkyl esters (e.g., sodium methyl-2-sulfo(C12-16) ester and disodium 2-sulfo(C12-C16)fatty acid available from Stepan Company under the trade designation ALPHASTEP PC-48) in combination with polyamine oxide film-forming polymers appear to increase the substantivity of a dried film of the antiseptic composition and adhesion of PSA-coated products. Certain of the sulfate and sulfonate containing surfactants also appear to significantly reduce dry times. The mechanism for this is not clear. While not intending to be bound by theory these surfactants may associate with cationic amine groups on film-forming polymers forming a more hydrophobic complex during dry down. Sulfates and sulfonates, phosphates and phosphonates, as well as the sulfobetaine type surfactants have been shown to reduce the dry time significantly.

Vehicles

Suitable vehicles (preferably liquid vehicles at 23° C. for certain embodiments) for the antiseptic compositions of the present invention include vehicles in which the monosaccharide and/or sugar alcohol are soluble, forming a clear and transparent solution having a percent transmission at 550 nanometers (nm) of greater than 85% in a cuvette with a path length of 1 centimeter (cm) at room temperature. The test solution is the composition less the antimicrobial agent and any thickener or film-forming polymer as well as the surfactant and any other insoluble species such as fillers or other particulates. Preferred compositions are stable and still clear after standing for 2 weeks at 23 C. Thus, to ensure solubility of the monosaccharide and/or sugar alcohol the vehicles generally include water, acetone, an alcohol (particularly a (C1-C4)alcohol (i.e., a lower alcohol) such as ethanol, 2-propanol, and n-propanol), or mixtures thereof.

Vehicles can include one or more humectants such as glycols, particularly polyalkylene glycols (e.g., polyethylene glycol, polypropylene glycol). In certain embodiments, the humectants (particularly polyalkylene glycols) are water-soluble, which means that when added to deionized water at 5% and mixed very well for 2 hours the percent transmission at 550 nm in a 1-cm path length cell is greater than 90%. In certain embodiments, the polyalkylene glycols having a molecular weight of less than 2500 daltons, preferably less than 1500 daltons, and more preferably less than 1000 daltons. Nonlimiting examples of preferred humectant-type glycol (polyols) include glycerol, polyglycerin, 1,3- and 1,4-butylene glycol, propylene glycol, dipropylene glycol, polypropylene glycol, polyethylene glycol, sorbitol, pantothenol, gluconic acid salts, and the like, including polyethoxylated derivatives thereof.

Preferred vehicles include purified water such as distilled and deionized water. Another preferred vehicle is polyethylene glycol (PEG), preferably having a weight average molecular weight of less than 1500 daltons, more preferably less than 1000 daltons, and even more preferably less than 600 daltons. It is recognized that these materials are comprised of a distribution of molecular weights. These materials have the following chemical structure: $H-(OCH_2CH_2)_n-OH$. Preferably these PEGs meet USP or NF specifications. Some sugar alcohols and monosaccharides may not be soluble in neat PEG. For example, xylitol at 5 wt-% will dissolve in PEG 400 if heated but this will phase out over a few days to weeks time. Thus, PEG-containing vehicles may need additional components to help the solubility such as water, another glycol, a surfactant, or a combination thereof. A preferred embodiment of the vehicle includes PEG and water.

For applications to intact skin, however, it may be desirable to include a lower alcohol such as ethanol, isopropanol, or n-propanol. These alcohols are well known to contribute to rapid microbial kill. For these applications the alcohol to water ratio is preferably at least 60:40, and more preferably at least 70:30, by weight. Addition of alcohol in these high concentrations will also decrease the dry time of the composition.

When a lower alcohol is used, incorporation of surfactants (as discussed in greater detail above) may or may not be necessary. In most cases reduction or elimination of the surfactant may allow for better adhesion of PSA-coated products over the dried film.

Particularly preferred antiseptic compositions for use on mucosal tissue include water and are substantially free (i.e., less than 10 wt-%) of volatile organic solvents (i.e., those having a closed-cap flash point of greater than 140° F. (60° C.)), such as acetone, lower alcohols, alkanes, volatile silicones, etc.

Aqueous formulations are preferred since these formulations are gentle to both skin and mucosal tissue and may even be suitable for use on open wounds as a wound cleanser. Furthermore, compositions containing organic solvents also may be flammable, which is typically a consideration in shipping and handling the product.

Preferred compositions of the present invention for use on mucosal tissue (oral, esophageal, nasal, anterior nares, vaginal, and wound) include less than 5 wt-% volatile organic solvents, and more preferably less than 3 wt-% volatile organic solvents, based on the total weight of the composition. These preferred aqueous compositions typically are nonflammable, having a closed-cup flash point of greater than 140° F. (60° C.). The addition of lower alcohols (C1-C4) at less than 4 wt-% may improve wetting of the compositions and yet maintain a flashpoint above 140° F. (60° C.). Flashpoint is measured according to test method ASTM D3278-96.

Optional Thickening Agents and Film-Forming Polymers

It is particularly desirable to add one or more thickening agents, particularly polymeric thickeners (which may be film-forming polymers), and/or film-forming polymers, to the antiseptic compositions to improve substantivity (e.g., resistance to wash off by blood and body fluid exposure), improve adhesion of PSA-coated products, increase viscosity to prevent dripping, etc., and/or reduce the tack of the compositions. Preferred polymeric thickeners and/or film-forming polymers of the antiseptic compositions of the present invention are substantive and resist removal by prolonged exposure to fluids such as water, saline, and body fluids, yet can be easily and gently removed without the need for organic solvents.

Certain skin antiseptic compositions of the present invention resist removal particularly well after they are dry. These compositions generally have lower viscosity (e.g., less than 1000 cps), and preferably greater than 10 cps, and have polymers with generally lower molecular weight (e.g., less than 200,000 daltons).

Antiseptic compositions for use on wound and mucosal tissues such as in the nose and anterior nares, however, have a higher viscosity in order to retain the composition on the tissue (which is often wet) longer and to prevent dripping and mess. These compositions preferably have a viscosity in excess of 100 cps, more preferably in excess of 500 cps, even more preferably in excess of 1000 cps, even more preferably in excess of 2000 cps, and even more preferably in excess of 5000 cps. These compositions may be thickened with one or more of the following:

a. Polymeric thickeners
   b. Hydrophobically modified polymeric thickeners
   c. Polymer/surfactant combinations
   d. Emulsifiers (including waxes)
   e. Inorganic colloidal thickeners Polymeric Thickeners for Topical Skin Antiseptics (e.g., Presurgical and IV Preps):

Preferred polymeric thickeners (which may be film-formers) have both hydrophilic and hydrophobic moieties. Particularly preferred polymeric thickeners include relatively high levels of total hydrophobic monomers. The preferred polymers are relatively hydrophobic to provide good substantivity and prolonged adhesion of PSA-coated products. Particularly preferred polymers are formed using a hydrophobic monomer level of at least 50 wt-%, and often as high as 80 wt-%, based on the total weight of the polymerizable composition (and preferably, based on the total weight of the polymer). Various combinations of hydrophobic monomers can be used if desired.

Examples of suitable hydrophobic and hydrophilic monomers are described in U.S. Pat. No. 6,838,078.

The polymeric thickeners (which may be film-forming polymers) can be nonionic, anionic, cationic, or zwitterionic. They may also have pressure sensitive adhesive properties. These include both synthetic and natural polymers as well as derivatives of natural polymers. Preferred polymers are cationic (particularly film-forming polymers).

Surprisingly, the solubility and stability of cationic polymeric thickeners are not affected detrimentally by the presence of multifunctional carboxylic acid containing hydroxy-acids such as citric acid, malic acid, tartaric acid, and the like. This is particularly surprising since it would be expected that adding these acids into compositions containing cationic polymers at very high concentrations would result in precipitation of the polymer due, for example, to ionic crosslinking.

In certain embodiments, preferred polymeric thickeners are cationic polymers, particularly those that include side-chain functional amine groups, which can be film-forming polymers. Examples of such groups include protonated tertiary amines, quaternary amines, amine oxides, and combinations thereof. Preferred such polymers are described in U.S. Pat. No. 6,838,078.

In certain embodiments, preferred polymeric thickeners are vinyl polymers prepared from amine group-containing monomers. Preferably, the vinyl polymers have a Tg of at least 30° C., and more preferably at least 50° C. One method of measuring the Tg of a polymer may involve the utilization of a Differential Scanning Calorimeter (DSC, e.g., the PYRIS 7-Series Thermal Analyzer, Perkin-Elmer, Shelton, Conn.) in the range of −100° C. to +100° C. at a rate of 20° C. per minute.

For certain preferred polymeric thickeners, the amine group-containing monomers can be used to prepare the polymers in an amount of at least 15 wt-%, more preferably at least 20 wt-%, even more preferably at least 25 wt-%, and most preferably at least 30 wt-%, based on the total weight of the polymerizable composition (and preferably, based on the total weight of the polymer). The amine group-containing monomers used to prepare the polymers are typically used in an amount of no greater than 70 wt-%, preferably no more greater than 65 wt-%, more preferably no greater than 60 wt-%, and most preferably no greater than 55 wt-%, based on the total weight of the polymerizable composition (and preferably, based on the total weight of the polymer).

The equivalent weight of the amine group contained in the polymer is preferably at least 300, more preferably at least 350, even more preferably at least 400, and most preferably at least 500, grams polymer per equivalent of amine group. The equivalent weight of the amine group contained in the polymer is preferably no greater than 3000, more preferably no greater than 1500, even more preferably no greater than 1200, and most preferably no greater than 950, grams polymer per equivalent of amine group.

Examples of polymeric thickeners that are film-forming polymers and that are PSAs at room temperature include those based on side-chain functional amine group monomers in combination with long chain alkyl acrylic polymers and optionally other hydrophilic monomers. For example, a particularly effective polymer that is a PSA includes 80% 2-ethylhexylacrylate and 20% trimethylaminoethyl methacrylate chloride, based on the total weight of the polymerizable composition (and preferably, based on the total weight of the polymer). Another PSA polymer in this class includes 75% 2-ethylhexyl acrylate, 25% trimethylaminoethyl methacrylate chloride, and 5% of a methoxy polyethylene glycol (9 ethyleneoxy units) monoacrylate, which is commercially available from Shin-Nakamura Chemicals, Wakayama City, Japan under the trade designation AM-90G.

For certain embodiments, preferably the viscosity of a composition of the present invention intended for use on topical skin is no greater than 1000 cps (and is preferably greater than 10 cps) when measured at 23° C. using a Brookfield RVT ROTOVISCO viscometer as described in the Examples. Therefore, useful polymers (preferably film-forming polymers) in the compositions of the present invention preferably have an inherent viscosity of no greater than 0.75, and more preferably no greater than 0.5 as measured in tetrahydrofuran according to the method in U.S. Pat. No. 7,147,873. In order to ensure sufficient substantivity, however, the inherent viscosity of the polymer (preferably film-forming polymer) is preferably at least 0.1, as measured in tetrahydrofuran according to the method in U.S. Pat. No. 7,147,873.

The molecular weight of the polymers is also preferably kept low in order to maintain a low viscosity composition for applications to tissue where the composition will dry such as skin. Preferably, the molecular weight of the polymers is generally no greater than 350,000 daltons, more preferably no greater than 250,000 daltons, even more preferably no greater than 150,000 daltons, and most preferably no greater than 100,000 daltons.

In certain embodiments, one or more polymeric thickeners and/or film-forming polymers (preferably substantive film-forming polymeric thickeners), are present in the antiseptic composition in a total amount of at least 2 wt-%, preferably at least 3 wt-%, and more preferably at least 5 wt-%, based on the total weight of antiseptic composition. In certain embodiments, one or more polymeric thickeners and/or film-forming polymers (preferably substantive film-forming polymeric thickeners), are present in the antiseptic composition in a total amount of no greater than 10 wt-%, and more preferably no greater than 8 wt-%, based on the total weight of antiseptic composition. The optional one or more polymeric thickeners and/or film-forming polymers (preferably substantive film-forming polymeric thickeners) are preferably present in an amount to provide a substantive composition.

Higher concentrations of film-forming polymers appear to promote adhesion of PSA-coated products. In certain compositions, however, higher concentrations may not be possible due to instability especially when exposed to temperatures above 50° C.

Preferably, in order to ensure adequate substantivity the weight ratio of film-forming polymer to hydroxycarboxylic acid is at least 0.25:1, preferably at least 0.35:1, more preferably at least 0.5:1, and most preferably at least 0.70:1.

Thickening of Mucosal and Wound Tissue Antiseptic Compositions:

As briefly described above, compositions for use on moist tissue, such as most mucosal and wound tissue, preferably are formulated to have a higher viscosity. These compositions may not dry out upon application and therefore, use of higher viscosity compositions may help to retain the composition on the tissue for longer periods of time. For example, when used in the nasal passages, the nasal cilia will try to flush the composition out of the nasal passages and down the throat. Similarly, when used in the oral cavity or esophageal cavity oral secretions will tend to flush the composition down the throat. Thus, it is advantageous to thicken these compositions in order to retain the antiseptic on the tissue for prolonged periods of time to ensure adequate antisepsis. These compositions may be thickened by means known in the art and in particular by use of one or more of the following: polymeric thickeners, inorganic colloidal thickeners, hydrophobically modified polymeric thickeners, polymer/surfactant combinations, emulsifiers, and combinations thereof.

Suitable polymeric thickeners are numerous and include nonionic, cationic, zwitterionic, and anionic natural gums and modified natural gums. These include those that can impart a gel-like viscosity to the composition, such as water-soluble or colloidally water-soluble polymers like cellulose ethers (e.g., methylcellulose, hydroxybutyl methylcellulose, hydroxypropylcellulose, hydroxypropyl methylcellulose, hydroxyethyl ethylcellulose and hydroxyethylcellulose), guar gum, starch and starch derivatives, arabia gum, tragacanth, galactan, carob gum, guar gum, karaya gum, carragheenin, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, as well as derivatives thereof. Cationic derivatives of cellulose and guar are particular preferred.

Useful herein are vinyl polymers such as polyvinyl alcohol, polyvinyl pyrrolidone, linear and crosslinked acrylic acid polymers such as those with the CTFA name CARBOMER, cationic polymers such as polyquaterium 4, 10, 24, 32, and 37 and other polymeric thickening agents disclosed in U.S. Pat. No. 6,582,711, polyacrylamide, acrylamide copolymers, polyethyleneimine.

Cationic natural polymer derivatives can be useful thickening agents for compositions of the present invention. Cationic modified cellulosic polymers are reported in the literature to be soluble in water. Such polymers have been found to be useful in the present invention. The most preferred modified cellulose products are sold under the trade names CELQUAT (National Starch and Chemicals Corp., Bridgewater, N.J.) and UCARE (Amerchol Corporation, Edison, N.J.). CELQUAT is a copolymer of a polyethoxylated cellulose and dimethyldiallyl ammonium chloride and has the Cosmetic, Toiletry and Fragrance Association (CTFA) designation Polyquaternium-4. A particularly suitable type of cationic polysaccharide polymer that can be used is a cationic guar gum derivative, such as guar hydroxypropyltrimonium chloride (commercially available from Rhone-Poulenc under the trade designation JAGUAR).

An alkyl modified quaternary ammonium salt of hydroxyethyl cellulose and a trimethyl ammonium chloride substituted epoxide can also be used. The polymer conforms to the CTFA designation Polyquaternium 24 and is commercially available as QUATRISOFT LM-200 from Amerchol Corp., Edison, N.J.

Soluble polymers, particularly cationic synthetic polymers can also be useful thickening agents. Synthetic cationic linear polymers useful in the present invention are preferably quite high in cationic charge density—generally having greater than 10 wt-% cationic monomer, preferably greater than 25 wt-%, and more preferably greater than 50 wt-%. This ensures a good cosmetic feel and may actually improve water solubility. In general, the polymers useful in the present invention have sufficient molecular weight to achieve thickening at generally less than 5 wt-% polymer, but not too high that the lotion/cream/ointment feels slimy and stringy. While the composition of the polymer will dramatically affect the molecular weight at which sufficient thickening will occur, the polymers preferably have a molecular weight of at least 150,000 daltons, and more preferably at least 250,000 daltons and most preferably at least 500,000 daltons. The polymers preferably have a molecular weight of no greater than 3,000,000 daltons, and more preferably no greater than 1,000,000 daltons. The homopolymers are preferably prepared from methacryloyloxyalkyl trialkyl ammonium salt, acryloyloxyalkyl trialkyl ammonium salt, and/or quaternized dialkylaminoalkylacrylamidine salt. Preferably, the polymers are copolymers of at least two monomers selected from the group consisting of trialkylaminoalkyl acrylate and methacrylate salts, dialkyldiallyl ammonium salts, acrylamidoalkyltrialkyl salts, methacrylamidoalkyltrialkyl salts, and alkyl imidazolinium salts, N-vinyl pyrrolidinone, N-vinyl caprolactam, methyl vinyl ether, acrylates, methacrylates, styrene, acrylonitrile, and combinations thereof. Typically, for the salts the counterions are preferably $F^-$, $Cl^-$, $Br^-$, and $CH_3(CH_2)_nSO_4^-$ where n=0-4.

A variety of quaternary copolymers of varying quaternization, can be synthesized based on homo or copolymers of amino acrylates with methyl, ethyl, or propyl side chains. These monomers could also be copolymerized with other nonionic monomers including quaternary acrylic homopolymers, such as homopolymers of 2-methacryloxyethyl trimethylammonium chloride and 2-methacryloxyethyl methyl diethyl ammonium bromide; and copolymers of quaternary acrylate monomers with a water-soluble monomer, such as Petrolite Product No. Q-0043, a proprietary copolymer of a linear quaternary acrylate and acrylamide at high molecular weight (4-5 million MW).

Another useful soluble cationic polymer is N,N-dimethylaminopropyl-N-acrylamidine (which is quaternized with diethylsulfate) bound to a block of polyacrylonitrile. This block copolymer is available under the trade designation Hypan QT-100 from Lipo Chemicals Inc., Paterson, N.J. It is quite effective at thickening aqueous systems and has a good cosmetic feel. This polymer as received, however, has an objectionable amine odor. The odor could probably be masked with the proper fragrance, but is preferably removed prior to formulation (e.g., with a solvent cleaning process) so that the formulation can be supplied without fragrance.

Suitable cationic polymers include, for example, copolymers of 1-vinyl-2-pyrrolidine and 1-vinyl-3-methyl-imidazolium salt (e.g., chloride salt), referred to in the industry by the Cosmetic, Toiletry, and Fragrance Association, (CTFA) as Polyquaternium-16. This material is commercially available from BASF Wyandotte Corp. (Parsippany, N.J.) under the LUVIQUAT tradename (e.g., LUVIQUAT FC 370); copolymers of 1-vinyl-2-pyrrolidine and dimethylaminoethyl methacrylate, referred to in the industry (CTFA) as Polyquaternium-11. This material is available commercially from Gaf Corp., Wayne, N.J., under the trade designation GAFQUAT; cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively.

Preferred natural or modified natural gums are cationic or zwitterionic. A particularly preferred polymer is available as CELQUAT SC230M (polyquarternium 10) available from National Starch Personal Care, Bridgewater, N.J.

Alternatively, crosslinked cationic polymers may be used such as those disclosed in U.S. Pat. No. 6,582,711.

Inorganic water-insoluble, but perhaps swellable, materials can be useful thickening agents for compositions of the present invention. These include, but are not limited to, bentonite, aluminum magnesium silicate, laponite, hectonite, fumed silica, precipitated silica, silica sols and other silica particulate as well as anhydrous silicic acid, and the like.

Hydrophobically modified polymeric thickeners can be useful thickening agents for compositions of the present invention. These are, in general, polymers comprising at least one C8 or longer alkyl or alkenyl group. These polymers tend to associate in solution and are often referred to as associative polymers. Associative polymers can be used in the thickening system of the compositions of the present invention. It is believed that such polymers thicken as a result of hydrophobic or Van der Waals association of hydrophobic side chains. Such associative polymers can form viscous to gelled solutions despite their relatively low molecular weights. Polymers that are soluble can be modified by the addition of a long chain hydrophobic group. A preferred class of such associative polymers is based on nonionic ethylenically unsaturated monomers wherein at least one comonomer has at least 8 carbon atoms.

An example is cetyl hydroxyethylcellulose, available as "NATROSOL PLUS" from Aqualon, which utilizes an associative mechanism to enhance the viscosity it produces. Grafted side chains of cetyl alkyl groups can associate with neighboring alkyl hydrophobes. These interpolymer associations can dramatically increase the viscosification efficiency of the polymer. In hydroalcoholic systems of the present invention, the interpolymer associations can be greatly improved if longer chain hydrophobic groups were used in place of the cetyl groups, since the C16 groups are not as insoluble as longer chain alkyls. For example, alkyl chains containing 18-31 carbon atoms, preferably 20-34 carbon atoms, provide particularly desirable polymeric thickeners in a hydroalcoholic solvent system containing at least a 65:35 alcohol to water ratio. Long chain alkenyl and aralkyl groups may also be suitable.

Polymer/surfactant combinations are also useful thickening agents for compositions of the present invention. These are discussed in detail in U.S. Pat. No. 5,908,619 as well as Novel Gelling Agents Based on Polymer/Surfactant Systems, E. D. Goodard et. al., J. Soc. Cosmet. Chem., 42, 19-34 (January/February, 1991) discloses polymer/surfactant thickener systems for completely aqueous systems based on quaternary polymers in combination with anionic surfactants. The thickening system includes a complex of a charged polymer and an oppositely charged surfactant. This complex is formed as a result of reaction between ionizable groups on both the polymer and the surfactant to form ionic groups on both, which then ionically associate. Preferably, this complex is formed as a result of acid-base reactions of the ionizable groups on the polymer and the surfactant. For example, the polymer can have acidic or basic groups that, when combined with a surfactant having acidic or basic groups neutralizes each other, thereby forming charged species. These charged species then ionically associate to form a complex that comprises the thickening system in the hydroalcoholic compositions of the present invention. The charged surfactant molecules can also hydrophobically associate as a result of the hydrophobic regions of the surfactant. U.S. Pat. No. 5,908,619 specifically refers to systems that utilize a hydroalcoholic vehicle. These same systems may be suitable for aqueous systems without alcohol utilizing ionizable which include hydrophobic side chains that are capable of hydrophobically associating with the ionizable surfactant and/or other hydrophobic side chains of other polymer molecules. Examples of suitable hydrophobic side chains include alkyl side chains having at least 8 carbon atoms, preferably at least 12 carbon atoms, and more preferably at least 16 carbon atoms, polystyrene side chains (typically of 2,000 to 30,000 number average molecular weight), and the like, and mixtures thereof.

Emulsifiers and waxes also may be used to thicken the compositions of the present invention. These systems tend to have an oil phase and a water phase and form a stable emulsion. In the case of biphasic formulations containing the above antimicrobial, the emulsifier and wax thickeners will be preferably employed in an amount within the range of from 3 weight percent (wt-%) to 14 wt-%, and more preferably from 5 wt-% to 10 wt-%, depending upon the amount of antiseptic and other surfactants employed.

The emulsifier-thickener suitable for use herein may comprise ethers of polyethylene glycol and fatty alcohols, such as non-ionic emulsifying waxes such as POLAWAX and POLAWAX A31 from Croda Co., which contain an alkyl alcohol such as cetyl and stearyl alcohol, in combination with one or more ethoxylated alcohols. A mixture of polyoxyethylene (20) stearyl alcohol ether (BRIJ 78, Uniqema) or Polyoxyethylene (20) cetyl alcohol ether (BRIJ 58, Uniqema) with cetyl or stearyl alcohol. The ratio of the BRIJ or a mixture of the two BRIJ with the fatty alcohol or a mixture of the two alcohols should be within the range of from 0.6 to 3.5, preferably from 1 to 3. Other suitable emulsifier systems include CRODAPHOS CES (Cetearyl Alcohol (and) Dicetyl Phosphate (and) Ceteth-10 Phosphate, Croda USA), Incroquat Behenyl TMS (behentrimonium methosulfate, cetearyl alcohol, Croda USA), non-ionic emulsifiers like polyoxyethylene oleyl ether, PEG-40 stearate, ceteareth-12 (e.g., EUMULGIN B-1 manufactured by Henkel), ceteareth-20 (e.g., EUMULGIN B-2 manufactured by Henkel), ceteareth-30, Lanette O (manufactured by Henkel; ceteareth alcohol), glyceryl stearate (e.g., CUTINA GMS manufactured by Henkel), PEG-100 stearate, ARLACEL 165 (glyceryl stearate and PEG-100 stearate, Uniqema), steareth-2 and steareth-20, or combinations/mixtures thereof, as well as cationic emulsifiers like stearamidopropyl dimethylamine and behentrimonium methosulfate, or combinations/mixtures thereof. Another emulsifier system suitable for use in the lotion or cream of the invention comprises a combination of glyceryl monostearate with polyoxyethylene sorbitan plamitate or stearate and cetyl or stearyl alcohol. For example, an oil in water cream can be made using castor oil (4.5-6%), glyceryl monostearate (4.5-6%), cetyl or stearyl alcohol (9-11%) and TWEEN 60 (polyoxyethylene sorbitan monostearate 2.7-3.5%).

Various combinations of thickening agents and/or film-forming polymers can be used in compositions of the present invention.

Other Optional Ingredients

It may be desirable to include one or more other (secondary) antimicrobial agents as preservatives and/or active ingredients in combination with iodine. Other actives can include cationics such as polyhexamethylene biguanide (PHMB, COSMOCIL CQ from Arch Biocides), chlorhexidine salts such as chlorhexidine gluconate, chlorhexidine acetate and the like, as well as other cationic antiseptics disclosed in U.S. Patent Application Publication No. 2006/0051384. Natural oil antiseptics such as those disclosed in U.S. Patent Application Publication No. 2006/0051384 may be added. In addition, it may be desirable to add antimicrobial lipids such as those described in U.S. Patent Application Publication No. 2005/0089539, although in certain embodiments, compositions of the present invention do not include antimicrobial lipids. Phenolic type antimicrobials also may be useful such as triclosan, parachlorometaxylenol and others disclosed in U.S. Patent Application Publication No. 2006/0052452.

It also may be desirable to add preservatives such as methyl, ethyl, propyl, and butyl paraben, 2 phenoxyethanol, hydantoins, diazolidinyl urea, and the like.

Compositions of the present invention may additionally employ adjunct components conventionally found in pharmaceutical compositions in their art-established fashion and at their art-established levels. Thus, for example, the compositions may contain additional compatible pharmaceutically active materials for combination therapy (such as supplementary antimicrobials, anti-parasitic agents, antipruritics, astringents, local anaesthetics, or anti-inflammatory agents), or may contain materials useful in physically formulating various dosage forms of the present invention, such as excipients, dyes, perfumes, lubricants, stabilizers, skin penetration enhancers, preservatives, or antioxidants, flavorants, flavor masking agents, odor masking agents, antiinflammatories, antioxidants, vitamins, enzymes, enzyme inhibitors, growth factors, and sensates to induce a cool or warm feeling such as menthol, and the like.

Methods of Use

Tissue antiseptic compositions of the present invention can be used in a variety of methods to disinfect tissue (particularly skin or mucosal tissue, such as oral tissue and esophageal tissue). For example, the compositions can be used to decolonize the nasal passages of a subject, which means to reduce the amount of bacteria therein. This may involve killing the bacteria, but this is not always necessary as long as they are reduced to a level that helps reduce the chance of a surgical site infection and/or reduces the risk of transmitting bacteria such as methicillin resistant *Staphylococcus aureus* (MRSA) between patients and healthcare staff. Typically, such methods occur simply by applying the composition to the tissue of a subject. Such methods of disinfecting tissue are preferably carried out prior to an invasive procedure (e.g., surgical procedure) being performed on the subject or to prevent transmission of bacteria such as MRSA between patients. For example, a composition of the present invention may be applied directly to the tissue or it may be impregnated into a substrate such as a swab, foam, wipe, etc., that is then applied to the nose optionally with some scrubbing or wiping action. The substrate is either removed immediately or optionally allowed to remain in place for a period of time before removing (e.g., 15-60 minutes).

Preferred Embodiments

The present invention provides the following numbered embodiments:

1. A tissue antiseptic composition comprising: an antimicrobial agent selected from the group consisting of iodine ($I_2$), an iodophor, and a combination thereof, wherein the antimicrobial agent is present in a sufficient concentration to provide an available iodine concentration of 0.1 wt-% to 2 wt-%; a monosaccharide, a sugar alcohol, or a combination thereof; and a vehicle that is a liquid at 23° C.; wherein the composition is a liquid at 23° C.
2. The tissue antiseptic composition of embodiment 1 further comprising an alpha-hydroxyacid.
3. The tissue antiseptic composition of embodiment 2 wherein the alpha-hydroxyacid is present in an amount greater than 1 wt-%.
4. The tissue antiseptic composition of embodiment 3 wherein the alpha-hydroxyacid is present in an amount greater than 3 wt-%.
5. The tissue antiseptic composition of embodiment 4 wherein the alpha-hydroxyacid is present in an amount greater than 5 wt-%.
6. The tissue antiseptic composition of any one of embodiments 1 through 5 further comprising a surfactant.
7. The tissue antiseptic composition of embodiment 6 comprising a mixture of surfactants.
8. The tissue antiseptic composition of embodiment 6 or embodiment 7 wherein the surfactant comprises an anionic surfactant, a zwitterionic surfactant, or a combination thereof.
9. The tissue antiseptic composition of embodiment 8 wherein the composition further comprises a nonionic surfactant in combination with an anionic surfactant or a zwitterionic surfactant.
10. The tissue antiseptic of embodiment 8 or embodiment 9 wherein the composition comprises a zwitterionic surfactant.
11. The tissue antiseptic of embodiment 10 wherein the zwitterionic surfactant comprises a sultaine, betaine, phospholipid, or a combination thereof.
12. The tissue antiseptic of embodiment 11 wherein the zwitterionic surfactant comprises a sultaine, phospholipid, or a combination thereof.
13. The tissue antiseptic of embodiment 8 or embodiment 9 wherein the composition comprises an anionic surfactant.
14. The tissue antiseptic of embodiment 13 wherein the anionic surfactant comprises a phosphate, phosphonate, sulfate, sulfonate, or a combination thereof.
15. The tissue antiseptic composition of embodiment 6 or embodiment 7 wherein the composition comprises a nonionic surfactant.
16. The tissue antiseptic composition of any one of embodiments 1 through 15 wherein the vehicle comprises water.
17. The tissue antiseptic composition of any one of embodiments 1 through 16 wherein the vehicle comprises a glycol.
18. The tissue antiseptic composition of embodiment 17 wherein the glycol comprises glycerol, polyglycerin, 1,3- and 1,4-butylene glycol, propylene glycol, dipropylene glycol, polypropylene glycol, polyethylene glycol, sorbitol, pantothenol, gluconic acid salts, polyethoxylated derivatives thereof, or a combination thereof.
19. The tissue antiseptic composition of embodiment 18 wherein the vehicle comprises a polyethylene glycol having a molecular weight of less than 1500.
20. The tissue antiseptic composition of embodiments 1 through 19 wherein the vehicle comprises a polyethylene glycol or a polyol in the greatest amount.
21. The tissue antiseptic composition of any one of embodiments 1 through 20 which is free of an antimicrobial lipid.

22. The tissue antiseptic composition of any one of embodiments 1 through 21 wherein the composition includes a sugar alcohol.
23. The tissue antiseptic composition of embodiment 22 wherein the sugar alcohol is an alcohol of a monosaccharide.
24. The tissue antiseptic composition of embodiment 23 wherein the alcohol of a monosaccharide comprises xylitol, sorbitol, mannitol, maltitol, erythritol, or a combination thereof.
25. The tissue antiseptic composition of any one of embodiments 1 through 24 having a viscosity of less than 1000 cps.
26. The tissue antiseptic composition of any one of embodiments 1 through 25 having a viscosity of greater than 10 cps.
27. The tissue antiseptic composition of embodiment 26 having a viscosity of greater than 100 cps.
28. The tissue antiseptic composition of embodiment 27 having a viscosity of greater than 500 cps.
29. The tissue antiseptic composition of embodiment 28 having a viscosity of greater than 1000 cps.
30. The tissue antiseptic composition of any one of embodiments 1 through 29 further comprising a thickener.
31. The tissue antiseptic composition of embodiment 30 wherein the thickener comprises a cationic polymer.
32. The tissue antiseptic composition of embodiment 30 wherein the thickener comprises a polysaccharide, modified polysaccharide, a polymer derived from a vinylpyrrolidone, or a combination thereof.
33. The tissue antiseptic composition of embodiment 32 wherein the thickener comprises a modified cellulose, guar, or a combination thereof.
34. The tissue antiseptic composition of embodiment 32 wherein the thickener comprises a polyvinylpyrrolidone or a vinylpyrrolidone copolymer.
35. The tissue antiseptic composition of any one of embodiments 1 through 34 which reduces normal skin flora by at least 1 log in 2 minutes on dry human skin site using ASTM testing method E1173-93 and a 30-second scrub with gauze soaked in the composition using moderate pressure.
36. The tissue antiseptic composition of any one of embodiments 1 through 35 which is stable at 50° C. for greater than 7 days with no visible changes.
37. A tissue antiseptic composition comprising: an antimicrobial agent selected from the group consisting of iodine ($I_2$), an iodophor, and a combination thereof, wherein the antimicrobial agent is present in a sufficient concentration to provide an available iodine concentration of 0.1 wt-% to 2 wt-%; a monosaccharide, a sugar alcohol, or a combination thereof; a surfactant; and a vehicle comprising a major amount of a water-soluble glycol humectant; wherein the composition is a liquid at 23° C.
38. The tissue antiseptic composition of embodiment 37 comprising a mixture of surfactants.
39. The tissue antiseptic composition of embodiment 37 or embodiment 38 wherein the surfactant comprises an anionic surfactant, a zwitterionic surfactant, or a combination thereof.
40. The tissue antiseptic composition of embodiment 39 wherein the composition further comprises a nonionic surfactant in combination with an anionic surfactant or a zwitterionic surfactant.
41. The tissue antiseptic of embodiment 39 or embodiment 40 wherein the composition comprises a zwitterionic surfactant.
42. The tissue antiseptic of embodiment 41 wherein the zwitterionic surfactant comprises a sultaine, betaine, phospholipid, or a combination thereof.
43. The tissue antiseptic of embodiment 42 wherein the zwitterionic surfactant comprises a sultaine, phospholipid, or a combination thereof.
44. The tissue antiseptic of embodiment 39 or embodiment 40 wherein the composition comprises an anionic surfactant.
45. The tissue antiseptic of embodiment 44 wherein the anionic surfactant comprises a phosphate, phosphonate, sulfate, sulfonate, or a combination thereof.
46. The tissue antiseptic composition of embodiment 37 or embodiment 38 wherein the composition comprises a nonionic surfactant.
47. The tissue antiseptic composition of any one of embodiments 37 through 46 wherein the vehicle comprises a polyethylene glycol having a molecular weight of less than 1500.
48. The tissue antiseptic composition of embodiment 47 wherein the vehicle comprises a polyethylene glycol having a molecular weight of less than 1000.
49. The tissue antiseptic composition of any one of embodiments 37 through 48 comprising a monosaccharide, an alcohol of a monosaccharide, or a combination thereof.
50. The tissue antiseptic composition of embodiment 49 wherein the composition includes an alcohol of a monosaccharide.
51. The tissue antiseptic composition of embodiment 50 wherein the alcohol of a monosaccharide comprises xylitol, sorbitol, mannitol, maltitol, erythritol, or a combination thereof.
52. The tissue antiseptic composition of any one of embodiments 37 through 51 further comprising an alpha-hydroxyacid.
53. The tissue antiseptic composition of embodiment 52 wherein the alpha-hydroxyacid is present in an amount greater than 1 wt-%.
54. The tissue antiseptic composition of embodiment 53 wherein the alpha-hydroxyacid is present in an amount greater than 3 wt-%.
55. The tissue antiseptic composition of embodiment 54 wherein the alpha-hydroxyacid is present in an amount greater than 5 wt-%.
56. The tissue antiseptic composition of any one of embodiments 37 through 55 wherein the vehicle further comprises water.
57. The tissue antiseptic composition of any one of embodiments 37 through 56 wherein the vehicle further comprises a (C1-C4)alcohol, or a mixture thereof.
58. The tissue antiseptic composition of any one of embodiments 37 through 57 wherein the vehicle is a liquid at 23° C.
59. The tissue antiseptic composition of any one of embodiments 37 through 58 which is free of an antimicrobial lipid.
60. A tissue antiseptic composition comprising: an antimicrobial agent selected from the group consisting of iodine ($I_2$), an iodophor, and a combination thereof, wherein the antimicrobial agent is present in a sufficient concentration to provide an available iodine concentration of 0.1 wt-% to 2 wt-%; a monosaccharide, a sugar alcohol, or a combination thereof; and a vehicle; wherein the composition has a viscosity of greater than 1000 cps; and wherein the composition is a liquid at 23° C.

61. A method of decolonizing the nasal passages of a subject, the method comprising applying the composition of any one of embodiments 1 through 60 to the nasal passages of the subject.
62. A method of disinfecting the tissue of a subject, the method comprising applying the composition of any one of embodiments 1 through 60 to the tissue of the subject.
63. The method of embodiment 62 wherein the tissue comprises mucosal tissue.
64. The method of embodiment 63 wherein the mucosal tissue comprises oral tissue.
65. The method of embodiment 64 wherein the oral mucosal tissue comprises esophageal tissue.
66. The method of embodiment 62 wherein the tissue comprises skin.
67. The method of any one of embodiments 61 through 66 wherein applying the composition to the tissue of a subject occurs prior to an invasive procedure being performed on the subject.
68. The tissue antiseptic composition of embodiment 24 wherein the alcohol of a monosaccharide is present in an amount greater than 0.5%.

EXAMPLES

Objects and advantages of this invention are further illustrated by the following examples, but the particular materials and amounts thereof recited in these examples, as well as other conditions and details, should not be construed to unduly limit this invention.

| | GLOSSARY | |
|---|---|---|
| LMDO | AMMONYX LMDO, lauramidopropyldimethylamine oxide, 30% solids solution | Stepan, Northfield, Il. |
| Tartaric acid | Tartaric acid | Sigma-Aldrich Fine Chemicals, Inc., Milwaukee, WI |
| HPMC | Klucel Pharma, hydroxypropylcellulose | Hercules, Aqualon div., Wilmington, DE |
| NaOH | sodium hydroxide | Sigma-Aldrich Fine Chemicals, Inc. |
| PLURONIC | PLURONIC block copolymer of poly(ethylene oxide) and poly(propylene oxide) | BASF Corporation |
| PVP-I | povidone-iodine USP | BASF Corporation |
| LA | L lactic acid, High Pure 88, USP | Purac America, Lincolnshire IL |
| MLA | DL malic acid | Universal Preserv-a-Chem, Edison, NJ |
| DI water | deionized water | |
| SB50 | MACKAM SB-50, lauramidopropylhydryoxysultaine, 50% solids solution | Mcintyre Group, University Park, Il |
| SG | CRODAFOS SG, PPG-5-ceteth-10 phosphate | Croda, Inc., Edison, NJ |
| Xylitol | Xylitol | Sigma Aldrich Fine Chemicals Inc., Milwauke, WI |
| PEG400 | Carbowax 400, Polyethylene glycol, MW = 400 | Dow Chemical, Midland MI |
| PVP K90 | PVP K90, polyvinylpyrolidone | International Specialty Products, ISP corp., Wayne, NJ |
| Irgasan DP300 | Triclosan | Ciba Specialty Chemicals, Tarrytown, NJ |
| Brij 700 | BRIJ 700 | Croda, Inc., Edison, NJ |
| Celquat SC-230M | Polyquaternium-10 | National Starch, Bridgewater, NJ |

Human Skin Antimicrobial Activity

Many of the compositions were checked for antimicrobial activity in a method similar to ASTM testing method E-1173-93 Standard Test for Evaluation of a Pre-operative Skin Preparation except that the compositions were applied to the backs (considered a "dry" site) of healthy volunteers and the baseline bacterial flora counts as put forth in section 7.1 of the ASTM method were not as high. Preps were always compared to the 2-step application of BETADINE Surgical Scrub (7.5% povidone-iodine, Purdue Frederick Company, Norwalk, Conn.) and BETADINE Surgical Solution (10% povidone-iodine "paint", Purdue Frederick Company, Norwalk, Conn.) or 3M One-Step Prep (3M Company, St. Paul, Minn.) per the manufacturer's instructions. All studies were randomized block designs. On the Study Day, two samples for baseline microbial counts were taken, one from the upper back and one from the lower back, on opposite sides of the spine. The test formulations and the control were randomized on the back-usually four across the upper back and four across the lower back. The residual bacteria were sampled from all sites 2.0 minutes after completion of application. All test samples were applied using sterile gauze saturated with the test composition (fully wet and dripping) applied in the following manner. In one method an approximately 2×2 inch (5.1 cm×5.1 cm) area was "scrubbed" for 60 seconds using moderate pressure. BETADINE Surgical Scrub and BETADINE Surgical Solution were applied following manufacturer's directions. Briefly, BETADINE Surgical Scrub was applied with saturated gauze and scrubbed for 5 minutes, wiped off; and the BETADINE Surgical Solution applied in an outward spiral from center. The compositions of the invention, therefore, had a much shorter time to kill than did the BETADINE scrub and paint procedure. A minimum of 8 subjects were used in accordance with sections 8.2-8.3 of ASTM testing method E1173. All subjects refrained from using antimicrobial products for a minimum of 2 weeks. The test compositions were applied using a 2×2 inch (5×5 cm) 2.5-cm thick piece of Wilsorb polyurethane open cell sponge (Wilsorb Flexible open cell polyurethane sponge, Illbruck Inc. polyurethane polyester, polyurethane sponge foam; Density=1.8 lb/ft$^3$ (ASTM 3574); Compressive force=0.56 psi at 25% compression or 0.81 psi at 65% compression). The average log reduction from baseline was determined for each composition. If multiple sites were run the log reduction for each site was determined. Results are reported in average log reductions (numerical average of the log reduction values). Note that an appropriate neutralizer was first determined for each formulation tested in accordance with ASTM testing method E1173-93 section 6.7. For most polymer systems the following neutralizing sampling solution was used: 0.4 g potassium dihydrogen phosphate, 10.1 g sodium hydrogen phosphate, 1.0 g TRITON X100 surfactant available from Union Carbide Corp., Houston Tex., 4.5 g lecithin (CAS #8002-43-5, available from Fisher Scientific, Fairlawn, N.J. as Cat No. 03376-250), 45.0 g TWEEN 80 (ICI), 1.0 g sodium thiosulfate, and deionized water to bring the total volume to 1 liter. The sampling solution was prepared by adding all components together and heating with stirring to approximately 60° C. until dissolved. It was then placed in containers and steam sterilized.

Certain of the quaternary polymers have been shown to have antimicrobial activity and require appropriate neutralizers as described herein. Polyanionic polymers such as polysulfonic acid polymers capable of precipitating out the quaternary polymers work well. The preferred polysulfonic acid polymers are available as AQ polyesters from Eastman Chemical Company, Kingston, Tenn., and particularly preferred is AQ 55S, which is reported to be a linear amorphous polyester based on sodium sulfoisophthalic acid. EASTMAN AQ 55S polymer is further described as a relatively high molecular weight having a dry Tg of about 55° C. This was dispersed in water at 30% by weight in water prior to addition to the naturalization media. When necessary, this was added to the sampling solution as 70 g of the 30% wt/wt solution of AQ55S in water prior to adjust the final volume to 1 liter with water.

Pig Urethra Assay

Inoculum Preparation: An inoculum of approximately $10^8$ tetracycline-resistant *S. aureus* (ATCC #27217) in phosphate buffered water, comparing to 0.5 McFarland Standard was prepared.

Test Method: Urethras were harvested from male and female pigs and frozen immediately at −20° C. When needed, a urethra was thawed slightly prior to testing allowing it to become flexible, but not soft. In a laminar flow hood the urethra was cleaned of fat and other tissue and cut into 1-centimeter segment tubes. These tubes were sliced in half to make two half cylinder segments. The urethras were allowed to reach room temperature before use. Each urethra segment was placed into a separate 50-mL sterile centrifuge tube and laid down on the interior side of the tube, near the opening, with the interior (mucosal) surface exposed.

Each urethra segment was inoculated with 10 microliters (µL) of the approximately $10^8$ inoculum prepared above. The centrifuge tube was capped and the tube was placed (still lying down) into 37° C. incubator for at least 30 minutes. This allowed the bacteria to attach to the tissue, thus making them more difficult to kill. Following the 30-minute attachment time, the centrifuge tubes were removed from the incubator.

A sample of 300-µL of each test composition was applied to each of two urethra segments (for duplicate testing) using either a positive displacement pipet or syringe. One pair of urethra segments was not prepped, but were used as positive controls. A forceps was used to manipulate the urethra segment so all surfaces are covered with the sample formulation (inside and outside). The centrifuge tube was capped once again and returned to the 37° C. incubator for the desired exposure time (30 minutes unless otherwise specified). The centrifuge tube was oriented in the incubator so the urethra segment stayed in contact with the test composition. After the exposure period the samples were removed from the incubator. The centrifuge tube was placed vertically in a tube rack and 25 mL of a sampling solution (see below) was added into the tube. The mixture was vortexed for 2 minutes at high speed to ensure excellent mixing and neutralization of the antiseptic. The sampling solution was previously tested to ensure proper neutralization of the antiseptic without damage to the bacteria cells, i.e., that the sampling solution is not toxic to the bacteria.

Note that an appropriate neutralizer was first determined for each formulation tested in accordance with ASTM testing method E1173-93 section 6.7. For most polymer systems the following neutralizing sampling solution was used: 0.4 g potassium dihydrogen phosphate, 10.1 g sodium hydrogen phosphate, 1.0 g TRITON X100 surfactant available from Union Carbide Corp., Houston Tex., 4.5 g soy refined lecithin (CAS #8002-43-5, available from Fisher Scientific, Fairlawn, N.J. as Cat No. 03376-250), 45.0 g TWEEN 80 (ICI), 1.0 g sodium thiosulfate, and deionized water to bring the total volume to 1 liter. The sampling solution was prepared by adding all components together and heating with stirring to approximately 60° C. until dissolved. The pH was 7.9. It was then placed in containers and steam sterilized. For samples that contained polyhexamethylene biguanide (PHMB, Cosmocil CQ) the neutralizing solution also contained 0.4% by weight poly(sodium 4-styrenesulfonate) (i.e., 4 g/L, Sigma Aldrich, Milwaukee, Wis., 70,000 MW, CAS #25704-18-1.

The neutralized sample was serially diluted with phosphate buffered water to $10^{-3}$. Each dilution was plated in duplicate using pour plating technique with Tryptic Soy Agar. In order to select for only the test bacteria (tetracycline-resistant *S. aureus* (ATCC #27217)), tetracycline was added to the agar prior to pouring the plates. Tetracycline was prepared at 4 mg/mL in sterile water and this preparation added to the agar at 1 mL tetracycline preparation per 1 L of agar. The agar plates were allowed to set, and then placed in a 37° C. incubator for 48 hours.

The plates were removed and the colony forming units, CFUs enumerated. The CFU found was multiplied by the dilution. A $log_{10}$ recovery of CFUs was determined by averaging the duplicate plates. If the values were not close (e.g., within 0.5 log) additional replicates were tested. The $log_{10}$ average of the control also was determined. A log reduction was determined by taking the difference between the log recovery of the control (typically about 6 logs) and subtracting the log recovery of the test composition.

Brookfield Viscosity Test

The viscosity was measured using a Brookfield RVT ROTOVISCO viscometer commercially available from Engineering Labs Inc. (Middleboro, Mass.) with a small sample adapter (ULA adapter) LVDVI+. Measurements were taken at 23° C.-25° C. using spindle size 00 at a speed of 30 revolutions per minute (rpm) for low viscosity samples. For samples having a viscosity greater than 1000 the viscosity was measured at 23° C. at ambient pressure using a Brookfield LVDV-I$^+$ viscometer equipped with a model D Brookfield heliopath and T spindles B-F. The spindle and speed was chosen for each particular sample such that the viscometer was operating in the middle of its range. All samples were allowed to equilibrate at 23° C. for 24 hours prior to measurement. Preferably the viscosity is taken at the lowest speed possible while staying within 20-80% of the viscometer range and more preferably between 30-70% of the range. In all cases, the sample size and container geometry were chosen to ensure that there were no wall effects. By "wall effects" it is meant the viscosity value is not affected by the container and is essentially equivalent to the viscosity taken in an infinitely large container. For this reason, lower viscosity samples required a larger sample size to accommodate the larger spindles. The following Table 1 outlines the preferred spindles for various sample viscosities, although the largest spindle should be used for the sample size.

TABLE 1

| Sample Viscosity | T Spindle to Use |
|---|---|
| 1000-50,000 | A or B |
| 50,000-100,000 | C |
| 100,000-500,000 | D |
| 500,000-1,000,000 | E |
| 1,000,000-3,000,000 | F |

The viscosity of each sample was taken as the highest relatively stable reading achieved on the first path the spindle traversed using the heliopath adapter.

Examples 1-2 and Comparative Examples A-B

The compositions shown in Table 2 were prepared using the general procedure described below:

1. A 20% solids solution of povidone-iodine USP was prepared by dissolving 30 grams (g) PVP-I in 120 g deionized water by sealing in a jar and rolling the jar until the PVPI dissolved.
2. The surfactants (SG, LMDO, and Brij 700) were dissolved in the deionized water for Ex. 2 and Comp. Ex. B and in PEG400/water for Ex. 1 and Comp. Ex. A.
3. Malic acid and lactic acid were added and dissolved by rolling.
4. Xylitol was added and dissolved by heating to 70° C. for one hour and cooled by rolling.
5. Povidone iodine was added as a powder or as a solution and the solution mixed by rolling overnight.

The samples prepared formed smooth viscous gels that had good antimicrobial activity. The gels were placed on freshly cut beef roast slices having lean and fat sections at room temperature. The compositions were stained by addition of Hydroxypyrene trisulfonic acid dye. This fluorescent dye allowed complete visualization of the spreading properties of the compositions using a black (UV) light. Both compositions were observed to spread along the tissue over both lean and fat sections and especially wick into crevices. While both samples spread well, Example 3 was found to spread more rapidly than Example 4.

TABLE 2

Compositions of Examples 1-2 and Comparative Examples A and B

| Component | Example 1 | Comparative Example A | Example 2 | Comparative Example B |
|---|---|---|---|---|
| PVP-I powder | 5 | 5 | | |
| PVP-I, 20% solution prep | | | 25 | 25 |
| Crodaphos SG | 1 | 1 | 1 | 1 |
| Ammonyx LMDO | 0.75 | 0.75 | 0.75 | 0.75 |
| Brij 700 | 1.4 | 1.4 | 1.4 | 1.4 |
| Xylitol | 10 | | 10 | |
| Lactic Acid | 5 | 5 | 5 | 5 |
| Malic Acid | | | 2 | 2 |
| Tartaric acid | 2 | 2 | | |
| PEG 400 | 61.85 | 81.85 | | |
| Celquat SC-230M | | | 2.5 | 2.5 |
| PVP K-90 | 3 | | | |
| Water | 10 | | 52.35 | 62.35 |
| Viscosity (cps) | 8800 (Spindle T-D at 12 rpm) | 9625 (Spindle T-D at 6 rpm) | 68000 | 12080 (Spindle T-D at 12 rpm) |
| Urethra kill, avg log reduction, initial innoculum 6.24 log | 2.81 | 2.21 | 4.68 | 2.87 |

The compositions were evaluated for their antimicrobial activity using the urethra kill assay. The results are shown in Table 2. The results indicate that in both the PEG 400 and water vehicles the addition of xylitol significantly increased the bacterial kill. The boost in antimicrobial activity in the aqueous (water) vehicle (Example 2) was very pronounced.

Examples 3 and 4

The compositions shown in Table 3 were prepared and tested for spreading.

TABLE 3

| Component | Example 3 | Example 4 |
|---|---|---|
| PVP-I powder | 5 | |
| PVP-I, 20% solution prep | | 25 |
| Mackam SB50 | 2.5 | 2.5 |
| Ammonyx LMDO | | |
| Brij 700 | 0.75 | 0.75 |
| Xylitol | 10 | 10 |
| Lactic Acid | 5 | 5 |
| Malic Acid | 2 | 2 |
| PEG 400 | 81.75 | |
| PVP K-90 | 3 | |
| Klucel Pharma | | 2.5 |
| Water | | 52.25 |
| Urethra kill, avg log reduction, initial innoculum 6.24 log | 2.5 | 4.6 |

Examples 5-7 and Comparative Example C

The compositions shown in Table 4 were prepared using the general procedure described below:
1. A 20% solids solution of povidone-iodine USP was prepared by dissolving 30 g PVP-I in 120 g deionized water by sealing in a jar and rolling the jar until the PVPI dissolved.
2. The surfactants (Mackam SB-50, and Brij 700) were dissolved in the deionized water for Example 7 and Comp. Ex. C and in PEG400/water for Examples 5 and 6.
3. Malic acid and lactic acid were added and dissolved by rolling.
4. Xylitol was added and dissolved by heating to 70 C for one hour and cooled by rolling.
5. Povidone iodine was added as a powder or as a solution and the solution mixed by rolling overnight.

TABLE 4

Compositions of Examples 5-7 and Comparative Example C

| Component | Example 5 | Example 6 | Example 7 | Comparative Example C |
|---|---|---|---|---|
| PVP-I powder | 5 | 5 | | |
| PVP-I, 20% solution prep | | | 25 | |
| Mackam SB 50 | 2.5 | 2.5 | 2.5 | 2.5 |
| Brij 700 | 0.75 | 0.75 | 0.75 | 0.75 |
| Xylitol | 10 | 10 | 10 | 10 |

TABLE 4-continued

Compositions of Examples 5-7 and Comparative Example C

| Component | Example 5 | Example 6 | Example 7 | Comparative Example C |
|---|---|---|---|---|
| Lactic Acid | 5 | 5 | 5 | 5 |
| Malic Acid | | 2 | 2 | 2 |
| Carbowax 400 NF | 63.25 | 61.25 | | |
| Celquat SC-230M | | | 2.5 | 2.5 |
| Cosmocil CQ | 0.5 | 0.5 | | |
| Irgasan | | | 0.25 | 0.25 |
| PVP K-90 | 3 | 3 | | |
| Water | 10 | 10 | 52 | 77 |
| Viscosity (cps) | 2800 | 118,000 | | 100,100 (Spindle T-D at 1.5 rpm) |
| Urethra kill, avg log reduction, initial innoculum 6.24 log | 2.0 | Not performed | 3.30 | 2.08 |

The compositions were evaluated for their viscosity and antimicrobial activity using the urethra kill assay. The results are shown above in Table 4.

Examples 8-10

Example 2 was repeated except that the polymer concentration was adjusted, i.e. the concentration of Celquat SC230M was adjusted. The balance was replaced with water. The results are shown below in Table 5.

TABLE 5

| Example No. | Concentration of Celquat SC230M | Viscosity (cps) |
|---|---|---|
| 2 | 2.5 | 68000 |
| 8 | 1.4 | 12000 |
| 9 | 1.2 | 4850 |
| 10 | 1.0 | 3400 |

Examples 11-13

Example 7 was repeated except that the polymer concentration was adjusted, i.e. the concentration of Celquat SC230M was adjusted. The balance was replaced with water. The results are shown below in Table 6.

TABLE 6

| Example No. | Concentration of Celquat SC230M | Viscosity (cps) |
|---|---|---|
| 7 | 2.5 | 118000 |
| 11 | 1.4 | 14500 |
| 12 | 1.2 | 12000 |
| 13 | 1.0 | 3800 |

Human Skin Antimicrobial Activity:

Examples 5, 10, 13 and Comparative Example C with only 1% polymer (polymer was replaced with water) were tested for Human Skin Antimicrobial Activity according to the procedure described herein. The samples were compared to 3M One-Step Prep. The results are shown in Table 7.

TABLE 7

| Example No. | Log Reduction in Human Skin Antimicrobial Assay |
|---|---|
| 10 | 2.11 |
| 5 | 0.93 |
| 13 | 1.99 |
| Comparative Example C, 1% polymer | 1.49 |
| 3M One-Step Prep | 2.34 |

The results in Tables 4 and 7 indicate that the aqueous preps performed better on human skin than the PEG vehicle in this assay when measured on skin and checked 10 minutes after application. Examples 7 and 10 performed significantly better than Comparative Example C in the urethra assay and the Human Skin Antimicrobial Assay respectively.

Human Tissue Interaction:

Use in the nasal cavity: Samples 5, 7, and 10 were applied to the nares of a human volunteer. A sample of 0.25 mL of each composition was applied into both anterior nares and rubbed by massaging the nose for 15 seconds. The compositions were allowed to stay in the nares/nostril without removal. After 4 hours the next sample was evaluated. All of the samples were found to be non-irritating. Although an iodine odor was detectable the odor was not objectionable.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A tissue antiseptic composition comprising:
   an antimicrobial agent selected from the group consisting of iodine ($I_2$), an iodophor, and a combination thereof, wherein the antimicrobial agent is present in a sufficient concentration to provide an available iodine concentration of 0.1 wt-% to 2 wt-%;
   a sugar alcohol of a monosaccharide;
   a vehicle that is a liquid at 23° C. wherein the vehicle is water;
   a surfactant selected from the group consisting of an anionic surfactant, a zwitterionic surfactant, and a combination thereof; and
   a thickener;
   wherein the composition is a liquid at 23° C., has a pH of 2 to 6, and has a viscosity of no greater than 100,000 cps at 23° C.

2. The tissue antiseptic composition of claim 1 further comprising an alpha-hydroxyacid.

3. The tissue antiseptic composition of claim 2 wherein the alpha-hydroxyacid is present in an amount greater than 1 wt-%.

4. The tissue antiseptic composition of claim 3 wherein the alpha-hydroxyacid is present in an amount greater than 2.5 wt-%.

5. The tissue antiseptic of claim 1 wherein the zwitterionic surfactant comprises a sultaine, betaine, phospholipid, or a combination thereof.

6. The tissue antiseptic of claim 1 wherein the anionic surfactant comprises a phosphate, phosphonate, sulfate, sulfonate, or a combination thereof.

7. The tissue antiseptic composition of claim 1 wherein the composition further comprises a nonionic surfactant.

8. The tissue antiseptic composition of claim 1 wherein the vehicle further comprises a glycol.

9. The tissue antiseptic composition of claim 8 wherein the vehicle further comprises a polyethylene glycol having a molecular weight of less than 1500.

10. The tissue antiseptic composition of claim 1 which is free of an antimicrobial lipid.

11. The tissue antiseptic composition of claim 1 having a viscosity of less than 1000 cps.

12. The tissue antiseptic composition of claim 1 having a viscosity of greater than 10 cps.

13. The tissue antiseptic composition of claim 1 which reduces normal skin flora by at least 1 log in 2 minutes on dry human skin site using ASTM testing method E1173-93 and a 30-second scrub with gauze soaked in the composition using moderate pressure.

14. The tissue antiseptic composition of claim 1 which is stable at 50° C. for greater than 7 days with no visible changes.

15. The tissue antiseptic composition of claim 1 wherein the composition has a pH of 3 to 5.

16. The tissue antiseptic composition of claim 1 wherein the sugar alcohol is present in an amount of at least 1 wt-%, based on the total weight of the composition.

17. The tissue antiseptic composition of claim 16 wherein the sugar alcohol is present in an amount of at least 4 wt-%, based on the total weight of the composition.

18. The tissue antiseptic composition of claim 1 wherein the sugar alcohol is completely soluble with no solid dispersed therein.

19. The tissue antiseptic composition of claim 1 wherein the sugar alcohol is selected from xylitol, mannitol, and combinations thereof.

20. The tissue antiseptic composition of claim 1 having a viscosity of no greater than 50,000 cps at 23° C.

21. The composition of claim 1, wherein the sugar alcohol of a monosaccharide is present at a concentration of at least 0.25%.

22. A method of decolonizing the nasal passages of a subject, the method comprising applying the composition of claim 1 to the nasal passages of the subject.

23. A method of disinfecting the tissue of a subject, the method comprising applying the composition of claim 1 to the tissue of the subject.

24. A tissue antiseptic composition comprising:
an antimicrobial agent selected from the group consisting of iodine ($I_2$), an iodophor, and a combination thereof, wherein the antimicrobial agent is present in a sufficient concentration to provide an available iodine concentration of 0.1 wt-% to 2 wt-%;
a sugar alcohol of a monosaccharide;
a surfactant selected from the group consisting of an anionic surfactant, a zwitterionic surfactant, and a combination thereof;
a vehicle comprising water and a major amount of a water-soluble glycol humectant; and
a thickener;
wherein the composition is a liquid at 23° C., and has a pH of 2 to 6.

25. The tissue antiseptic composition of claim 24 wherein the composition further comprises a nonionic surfactant.

26. The tissue antiseptic composition of claim 24 wherein the glycol humectant is a polyethylene glycol having a molecular weight of less than 1500.

27. The tissue antiseptic composition of claim 24 further comprising an alpha-hydroxyacid.

28. The tissue antiseptic composition of claim 24 which is free of an antimicrobial lipid.

29. The tissue antiseptic composition of claim 24 wherein the composition has a pH of 3 to 5.

30. The tissue antiseptic composition of claim 24 wherein the sugar alcohol is present in an amount of at least 1 wt-%, based on the total weight of the composition.

31. The tissue antiseptic composition of claim 30 wherein the sugar alcohol is present in an amount of at least 4 wt-%, based on the total weight of the composition.

32. A method of decolonizing the nasal passages of a subject, the method comprising applying the composition of claim 24 to the nasal passages of the subject.

33. A method of disinfecting the tissue of a subject, the method comprising applying the composition of claim 24 to the tissue of the subject.

34. A tissue antiseptic composition comprising:
an antimicrobial agent selected from the group consisting of iodine ($I_2$), an iodophor, and a combination thereof, wherein the antimicrobial agent is present in a sufficient concentration to provide an available iodine concentration of 0.1 wt-% to 2 wt-%;
a sugar alcohol of a monosaccharide;
a vehicle wherein the vehicle is water;
a surfactant selected from the group consisting of an anionic surfactant, a zwitterionic surfactant, and a combination thereof; and
a hydroxycarboxylic acid;
wherein the composition has a viscosity of greater than 1000 cps and no greater than 100,000 cps at 23° C.; and
wherein the composition is a liquid at 23° C., and has a pH of 2 to 6.

35. The tissue antiseptic composition of claim 34 wherein the composition has a pH of 3 to 5.

36. The tissue antiseptic composition of claim 34 wherein the sugar alcohol is present in an amount of at least 1 wt-%, based on the total weight of the composition.

37. The tissue antiseptic composition of claim 36 wherein the sugar alcohol is present in an amount of at least 4 wt-%, based on the total weight of the composition.

38. A tissue antiseptic composition comprising:
an antimicrobial agent selected from the group consisting of iodine ($I_2$), an iodophor, and a combination thereof, wherein the antimicrobial agent is present in a sufficient concentration to provide an available iodine concentration of 0.1 wt-% to 2 wt-%;
xylitol;
a vehicle wherein the vehicle is water;
a surfactant selected from the group consisting of an anionic surfactant, a zwitterionic surfactant, and a combination thereof; and
a thickener;
wherein the composition is a liquid at 23° C., has a pH of 2 to 6, and has a viscosity of no greater than 100,000 cps at 23° C.

39. A tissue antiseptic composition comprising:
an antimicrobial agent selected from the group consisting of iodine ($I_2$), an iodophor, and a combination thereof, wherein the antimicrobial agent is present in a sufficient concentration to provide an available iodine concentration of 0.1 wt-% to 2 wt-%;
xylitol;

a vehicle wherein the vehicle is water;
a surfactant selected from the group consisting of an anionic surfactant, a zwitterionic surfactant, and a combination thereof; and
a hydroxycarboxylic acid;
wherein the composition has a viscosity of greater than 1000 cps and no greater than 100,000 cps at 23° C.; and
wherein the composition is a liquid at 23° C., and has a pH of 2 to 6.

40. A tissue antiseptic composition comprising:
an antimicrobial agent selected from the group consisting of iodine ($I_2$), an iodophor, and a combination thereof, wherein the antimicrobial agent is present in a sufficient concentration to provide an available iodine concentration of 0.1 wt-% to 2 wt-%;
a sugar alcohol of a monosaccharide;
a vehicle wherein the vehicle is water;
a surfactant selected from the group consisting of an anionic surfactant, a zwitterionic surfactant, and a combination thereof; wherein the anionic surfactant is selected from the group consisting of a phosphate, a phosphonate, a sulfate, a sulfonate, and a combination thereof; and
a thickener.

41. The tissue antiseptic of claim 40 wherein the surfactant is a zwitterionic surfactant.

42. The tissue antiseptic of claim 41 wherein the zwitterionic surfactant comprises a sultaine, betaine, phospholipid, or a combination thereof.

43. The tissue antiseptic of claim 40 wherein the surfactant is an anionic surfactant.

44. A method of decolonizing the nasal passages of a subject, the method comprising applying the composition of claim 40 to the nasal passages of the subject.

45. A method of disinfecting the tissue of a subject, the method comprising applying the composition of claim 40 to the tissue of the subject.

46. A tissue antiseptic composition comprising:
an antimicrobial agent selected from the group consisting of iodine ($I_2$), an iodophor, and a combination thereof, wherein the antimicrobial agent is present in a sufficient concentration to provide an available iodine concentration of 0.1 wt-% to 2 wt-%;
a sugar alcohol of a monosaccharide;
a vehicle wherein the vehicle is water;
a surfactant selected from the group consisting of a sultaine, a betaine, a phospholipid, a phosphate, a phosphonate, sulfate, a sulfonate, and a combination thereof; and
a thickener.

* * * * *

UNITED STATES PATENT AND TRADEMARK OFFICE
CERTIFICATE OF CORRECTION

PATENT NO. : 10,052,384 B2
APPLICATION NO. : 12/345085
DATED : August 21, 2018
INVENTOR(S) : Scholz It is certified that error appears in the above-identified patent and that said Letters Patent is hereby corrected as shown below:

On the Title Page

<u>Column 2 under item (56), (Other Publications)</u>
Line 1, delete "P. R. R" and insert -- P. R. --, therefor.

In the Specification

<u>Column 1</u>
Line 32, delete "precatherization" and insert -- precatheterization --, therefor.

<u>Column 5</u>
Line 35, delete "musocal" and insert -- mucosal --, therefor.

<u>Column 6</u>
Line 34, delete "and or" and insert -- and/or --, therefor.

<u>Column 7</u>
Line 66, delete "monosaccarides" and insert -- monosaccharides --, therefor.

<u>Column 8</u>
Line 4, after "ribose" insert -- . --.

<u>Column 10</u>
Line 21, delete "and or" and insert -- and/or --, therefor.

<u>Column 11</u>
Line 32, delete "Polaxamers. Surfactants" and insert -- Poloxamers surfactants --, therefor.

<u>Column 12</u>
Line 37, after "to:" delete "P".

Signed and Sealed this
Fifth Day of February, 2019

Andrei Iancu
*Director of the United States Patent and Trademark Office*

Line 60, delete "at lease" and insert -- at least --, therefor.

Column 13
Line 64, delete "ALPHASTE" and insert -- ALPHASTEP --, therefor.
Line 66, delete "LANTHANOL" and insert -- LATHANOL --, therefor.

Column 14
Line 5, delete "Phosponates." and insert -- Phosphonates. --, therefor.
Line 26, delete "CRODAPHOS" and insert -- CRODAFOS --, therefor.
Line 27, delete "Parsipanny," and insert -- Parsippany, --, therefor.

Column 19
Line 29 (approx.), delete "arabia" and insert -- arabic --, therefor.
Line 31 (approx.), delete "carragheenin," and insert -- carrageenan, --, therefor.
Line 44, delete "polyquaterium" and insert -- polyquaternium --, therefor.

Column 21
Line 4-5, delete "dimethyldiallyammonium" and insert -- dimethyldiallylammonium --, therefor.
Line 11, delete "(polyquarternium" and insert -- (polyquaternium --, therefor.
Line 18-19, delete "hectonite," and insert -- hectorite, --, therefor.

Column 22
Line 43, delete "CRODAPHOS" and insert -- CRODAFOS --, therefor.
Line 60, delete "plamitate" and insert -- palmitate --, therefor.

Column 27
Line 51 (approx.), delete "lauramidopropylhydryoxysultaine," and insert
-- lauramidopropylhydroxysultaine, --, therefor.
Line 55 (approx.), delete "Milwauke," and insert -- Milwaukee, --, therefor.
Line 58 (approx.), delete "polyvinylpyrolidone" and insert -- polyvinylpyrrolidone --, therefor.

Column 31
Line 21 (approx.), delete "Crodaphos" and insert -- Crodafos --, therefor.
Line 36 (approx.), delete "innoculum" and insert -- inoculum --, therefor.
Line 65 (approx.), delete "innoculum" and insert -- inoculum --, therefor.

Column 33
Line 19 (approx.), delete "innoculum" and insert -- inoculum --, therefor.